United States Patent
Kimura et al.

(10) Patent No.: US 7,389,673 B2
(45) Date of Patent: Jun. 24, 2008

(54) SENSOR FOR DETECTING ANALYTE IN LIQUID AND DEVICE FOR DETECTING ANALYTE IN LIQUID USING THE SAME

(75) Inventors: Tetsuya Kimura, Omihachiman (JP); Koji Fujimoto, Otsu (JP); Kenjiro Okaguchi, Moriyama (JP); Shinya Yamamoto, Otsu (JP); Ryoichi Morimoto, Yasu (JP); Toru Yabe, Konan (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 0 days.

(21) Appl. No.: 11/683,004

(22) Filed: Mar. 7, 2007

(65) Prior Publication Data

US 2007/0145862 A1 Jun. 28, 2007

Related U.S. Application Data

(63) Continuation of application No. PCT/JP2005/015185, filed on Aug. 22, 2005.

(30) Foreign Application Priority Data

Sep. 10, 2004 (JP) ............................. 2004-263952

(51) Int. Cl.
*G01N 29/036* (2006.01)
*H01L 41/08* (2006.01)

(52) U.S. Cl. ..................... 73/24.06; 73/24.01; 73/61.75; 73/64.53; 310/313 D; 310/313 B; 310/313 R

(58) Field of Classification Search .............. 73/24.01, 73/24.06, 61.75, 64.53; 310/313 R, 313 B, 310/313 D
See application file for complete search history.

(56) References Cited

U.S. PATENT DOCUMENTS

| | | | | |
|---|---|---|---|---|
| 4,312,228 A | * | 1/1982 | Wohltjen | ...................... 73/597 |
| 4,735,906 A | * | 4/1988 | Bastiaans | ..................... 436/527 |
| 4,895,017 A | * | 1/1990 | Pyke et al. | ................. 73/24.06 |

(Continued)

FOREIGN PATENT DOCUMENTS

JP           63-250560 A           10/1988

(Continued)

OTHER PUBLICATIONS

Official Communication for PCT Application No. PCT/JP2005/015185; mailed on Nov. 22, 2005.

*Primary Examiner*—Hezron E. Williams
*Assistant Examiner*—Rose M Miller
(74) *Attorney, Agent, or Firm*—Keating & Bennett, LLP

(57) ABSTRACT

A sensor for detecting an analyte in liquid includes a base substrate provided with openings and electrode lands on one surface thereof and SAW elements each provided with a sensing portion having at least one IDT electrode on one side. The SAW elements are mounted on the base substrate with bump electrodes by a flip-chip bonding method so that the sensing portions of the SAW elements face the openings of the base substrate. At least one of the sensing portions is coated with a reaction membrane which binds to an analyte.

11 Claims, 16 Drawing Sheets

U.S. PATENT DOCUMENTS

| | | | | |
|---|---|---|---|---|
| 5,220,234 | A | * | 6/1993 | Flory et al. ............. 310/313 D |
| 5,283,037 | A | * | 2/1994 | Baer et al. ............... 422/82.01 |
| 6,404,110 | B1 | * | 6/2002 | Nakashima et al. ......... 310/364 |
| 6,626,026 | B2 | * | 9/2003 | Banda et al. ............... 73/24.01 |
| 2005/0029906 | A1 | * | 2/2005 | Miyaji ........................ 310/348 |

FOREIGN PATENT DOCUMENTS

| | | | | |
|---|---|---|---|---|
| JP | 02-238357 | A | | 9/1990 |
| JP | 05-045339 | A | | 2/1993 |
| JP | 05045338 | A | * | 2/1993 |
| JP | 05-322736 | A | | 12/1993 |
| JP | 06-053773 | A | | 2/1994 |
| JP | 06-133759 | A | | 5/1994 |
| JP | 06194346 | A | * | 7/1994 |
| JP | 09243618 | A | * | 9/1997 |
| JP | 10090270 | A | * | 4/1998 |
| JP | 2764108 | B2 | | 6/1998 |
| JP | 2002-283293 | A | | 10/2002 |
| JP | 2003-502616 | A | | 1/2003 |
| JP | 2003115744 | A | * | 4/2003 |
| JP | 2003139746 | A | * | 5/2003 |
| JP | 2003294713 | A | * | 10/2003 |
| JP | 2004-045358 | A | | 2/2004 |
| JP | 2004-147220 | A | | 5/2004 |
| JP | 2004-153412 | A | | 5/2004 |
| JP | 2004-200908 | A | | 7/2004 |

* cited by examiner

SENSOR FOR DETECTING ANALYTE IN LIQUID AND DEVICE FOR DETECTING ANALYTE IN LIQUID USING THE SAME

BACKGROUND OF THE INVENTION

1. Field of the Invention

The present invention relates to sensors for detecting an analyte in liquid using SAW elements (surface acoustic wave elements), and also relates to devices for detecting an analyte in liquid including such sensors. More specifically, the present invention relates to sensors for detecting an analyte in liquid, each sensor includes at least one SAW element mounted on a base substrate via a bump electrode, and also relates to devices for detecting an analyte in liquid with the sensors.

2. Description of the Related Art

Various types of sensors for detecting analytes in liquids have been disclosed in the past.

For example, Japanese Unexamined Patent Application Publication No. 63-250560 (Patent Document 1) discloses a sensor for detecting an analyte in liquid using a surface acoustic wave. FIG. 23 is a schematic front cross-sectional view for illustrating the sensor disclosed in Patent Document 1.

A sensor 102 for detecting an analyte in liquid is immersed in a solution 101 containing an analyte. The sensor 102 is defined by a surface acoustic wave element. In other words, the sensor 102 includes a rectangular plate-like piezoelectric substrate 103, an input IDT electrode 104, and an output IDT electrode 105. The input IDT electrode 104 and the output IDT electrode 105 are arranged on the same surface of the piezoelectric substrate 103 with a predetermined distance therebetween. In addition, a membrane 106 for adsorbing an analyte is arranged between the input IDT electrode 104 and the output IDT electrode 105. A surface acoustic wave is excited in the piezoelectric substrate 103 by applying an alternating voltage to the input IDT electrode 104. The excited surface acoustic wave propagates toward the output IDT electrode 105. At the output IDT electrode 105, an electric signal based on the propagated surface wave is extracted. Since the membrane 106 adsorbs the analyte, the load to the surface of the piezoelectric substrate 103 due to the membrane 106 is changed when the analyte is present. Consequently, the propagating surface acoustic wave is modified by the presence of the analyte and, therefore, the output extracted from the output IDT electrode 105 is changed. Thus, the detection of the analyte and the measurement of concentration thereof are enabled.

However, in the measurement method using the sensor 102 for detecting an analyte in liquid, the sensor 102 must be immersed in a liquid 101. Therefore, when the amount of the liquid 101 containing the analyte is small, the analyte in the liquid cannot be detected.

Further, even if a large amount of a liquid is prepared, the measurement cost is disadvantageously high when the liquid is expensive.

In addition, in the sensor 102 for detecting an analyte in liquid, a liquid 101 adheres not only to regions where the surface acoustic wave propagates but also to regions where electrode pads or bonding wires, which are connected to the IDT electrodes 103 and 104, are disposed. Therefore, the electrical characteristic is disadvantageously changed so as to deteriorate the detection accuracy.

On the other hand, Japanese Unexamined Patent Application Publication No. 5-45339 (Patent Document 2) discloses a method for measuring an analyte in liquid without immersing a sensor for detecting an analyte in liquid.

In the sensor of Patent Document 2, an IDT electrode is disposed on a first principle surface of a piezoelectric substrate, and a measuring pond for receiving a liquid containing an analyte is formed on a second principle surface of the piezoelectric substrate, which is the opposite side of the first principle surface. Here, a liquid is injected into the measuring pond provided on the second principle surface, and the measurement is performed. Thus, it is not necessary to immerse the entire sensor in the liquid. Furthermore, since the IDT electrode is not brought into contact with the liquid, the electrical characteristic is not substantially changed.

As described above, in the sensor disclosed in Patent Document 2 for detecting an analyte in liquid, a large amount of liquid is not necessary. In addition, the liquid negligibly adheres to the IDT electrode.

However, in the sensor disclosed in Patent Document 2, a liquid containing an analyte is present on the second principle surface of the piezoelectric substrate. On the other hand, a surface acoustic wave propagates on the first principle surface of the piezoelectric substrate, namely, the surface acoustic wave propagates extremely close to the surface of the principle surface on which the IDT electrode is disposed. Therefore, when a solution is applied to the second principle surface, the surface acoustic wave propagating on the first principle surface is not substantially influenced by the change caused by the presence of the solution. Therefore, in the sensor disclosed in Patent Document 2, the detection accuracy cannot be sufficiently increased.

In addition, in the sensor disclosed in Patent Document 2, energy disperses not only to near the surface of the piezoelectric substrate but also to a certain depth of the piezoelectric substrate. The leak component of a propagating SH wave causes noise, and therefore, the measurement accuracy is disadvantageously decreased.

SUMMARY OF THE INVENTION

To overcome the problems described above, preferred embodiments of the present invention provide a sensor for detecting an analyte in liquid, which is not required to be immersed in a liquid containing the analyte and which accurately detects the analyte in a small amount of a liquid, and a device for detecting an analyte in liquid with the sensor.

A sensor for detecting an analyte in liquid according to a preferred embodiment of the present invention includes a base substrate, a piezoelectric substrate, and at least one SAW element disposed on the piezoelectric substrate. The base substrate is provided with at least one opening. On one surface of the base substrate, an electrode land is provided at the periphery of the opening. The SAW element includes at least one IDT electrode defining a sensing portion. The at least one SAW element is mounted on the base substrate so that the sensing portion of the at least one SAW element faces the at least one opening provided to the base substrate. In order to mount the SAW element on the base substrate, the sensor also includes a bump electrode connecting the SAW element to the electrode land of the base substrate. The sensor further includes a resin layer coating the circumferences of the SAW element and the bump electrode. Further, the surface of at least one sensing portion is coated with a reaction membrane which binds to an analyte.

In a preferred embodiment of the sensor for detecting an analyte in liquid according to the present invention, the SAW element is defined by a resonator-type SAW filter.

In another preferred embodiment of the sensor for detecting an analyte in liquid according to the present invention, the reaction membrane binds to a specific protein.

In another preferred embodiment of the sensor for detecting an analyte in liquid according to the present invention, the sensor is further provided with a first adhesion layer on a surface of the base substrate, wherein the surface is at the opposite side of the surface on which the SAW element is mounted.

In a further preferred embodiment of the sensor for detecting an analyte in liquid according to the present invention, the sensor is further provided with a first protecting member coating the first adhesion layer.

In another preferred embodiment of the sensor for detecting an analyte in liquid according to the present invention, the sensor is provided with a second protecting member fixed to a surface of the base substrate at the side on which the SAW element is mounted. The second protecting member includes a concave portion for receiving the SAW element.

In a further preferred embodiment of the sensor for detecting an analyte in liquid according to the present invention, the sensor is provided with a second adhesion layer between the base substrate and the second protecting member.

In a further preferred embodiment of the sensor for detecting an analyte in liquid according to the present invention, the first protecting member is provided with a liquid-supplying opening which is connected to the opening of the base substrate.

In another preferred embodiment of the sensor for detecting an analyte in liquid according to the present invention, the sensor is provided with a first channel connecting the liquid-supplying opening and the sensing portion of the SAW element.

In another preferred embodiment of the sensor for detecting an analyte in liquid according to the present invention, the first protecting member is provided with a liquid-discharging opening, and the sensor is further provided with a second channel connecting the liquid-discharging opening and the sensing portion of the SAW element.

A device for detecting an analyte in liquid according to a preferred embodiment of the present invention includes a sensor for detecting an analyte in liquid according to the present invention, an amplifier, a frequency counter, and a controller. The amplifier is connected to the sensor and amplifies output from the sensor.

In an example of the sensor for detecting an analyte in liquid according to a preferred embodiment of the present invention, a plurality of SAW elements are mounted on one side of a base substrate via bump electrodes so that a sensing portion faces an opening of the base substrate. The circumferences of the SAW elements and the bump electrodes are coated with a resin layer, but the resin layer is provided so that the sensing portion is exposed to the opening. Further, the surface of the at least one sensing portion is coated with a reaction membrane.

Therefore, in the measurement, a liquid containing an analyte may be injected into the opening of the base substrate from the side opposite to the side on which the SAW elements are mounted. In other words, it is not necessary to immerse the entire sensor in a large amount of a liquid. Therefore, the analyte in liquid can be detected using a small amount of a liquid.

During detection, a liquid injected into the opening adheres to the sensing portion, which faces the opening, of at least one of the SAW elements. Since the reaction membrane is disposed above the surface of the sensing portion of the at least one SAW element, when the analyte binds to the reaction membrane, the load caused by the reaction membrane is changed. Therefore, based on the change in the load, the presence of the analyte and the concentration thereof can be measured.

In preferred embodiments of the present invention, the sensing portion of the SAW element is present at the side of the surface on which the surface acoustic wave propagates, and a liquid containing an analyte directly adheres to the reaction membrane which is disposed above the sensing portion. Therefore, the sensitivity of the sensor in measuring the analyte is effectively increased.

Consequently, an analyte in liquid can be measured by using a small amount of a liquid with high accuracy and sufficient sensitivity.

When a resonator-type SAW filter is used as the SAW element, the sensor can be miniaturized as compared to a case in which a transversal filter is used. In addition, the insertion-loss is significantly reduced, which allows a decrease in the amplification degree of an amplifier. Consequently, the electric power consumption is decreased.

When the reaction membrane is one that binds to a specific protein, the existence or nonexistence of the specific protein and the concentration thereof can be detected or measured with high accuracy according to various preferred embodiments of the present invention.

When the sensor is further provided with a first adhesion layer on the base substrate at the side opposite to the surface on which the SAW element is mounted, the circumference of the opening where the sensing surface of the SAW element exposes is coated with the first adhesion layer. Therefore, contamination of the upper surface of the base substrate is prevented. In particular, when an elastic material, such as a rubber sheet, is used as the first adhesion layer, the base substrate and the adhesion layer can be adhered to each other by only pushing the sensor from the base substrate side. Therefore, the leakage of a liquid is securely prevented. In addition, the volume of a trapped liquid can be controlled by controlling the thickness of the first adhesion layer.

Further, when the sensor is provided with a first protecting member coating the first adhesion layer, the volume of an opening provided to the first protecting member and being connected to the opening of the base substrate can be increased by controlling the thickness of the first protecting member. As a result, an increased amount of a liquid can be supplied to the sensing portion.

When the sensor is further provided with a second protecting member having a concave portion for receiving the SAW element and being fixed to the base substrate at the side on which the SAW element is mounted, the second protecting member protects the SAW element mounted on the base substrate.

When the sensor is provided with a second adhesion layer between the base substrate and the second protecting member, the adhesion strength between the second protecting member and the base substrate is effectively increased by the second adhesion layer.

When the first protecting member is provided with a liquid-supplying opening and the liquid-supplying opening is connected to the opening of the base substrate, an increased amount of a liquid can be supplied to the sensing portion of the SAW element.

When the sensor is provided with a first channel connecting the liquid-supplying opening and the sensing portion of the SAW element, the liquid-supplying opening can be arranged at a position which is different from the position of the sensing portion in the surface direction. Thus, flexibility in the design is increased. In addition, a liquid injected into the liquid-supplying opening can be rapidly transferred to the sensing portion.

When the sensor is provided with a liquid-discharging opening to the first protecting member and with a second channel for connecting the sensing portion and the liquid-discharging opening, a liquid used for the measurement of an analyte can be rapidly discharged to the outside from the sensing portion through the liquid-discharging opening.

A device for detecting an analyte in liquid according to preferred embodiments of the present invention includes a sensor for detecting an analyte in liquid according to preferred embodiments of the present invention, an amplifier for amplifying output from the sensor, a frequency counter, and a controller. The sensor outputs a frequency signal based on the presence of an analyte or concentration of an analyte. The frequency signal is amplified by the amplifier and counted by the frequency counter. Thus, since the sensor according to preferred embodiments of the present invention is used in the device, the presence of the analyte and/or the concentration thereof can be determined with high accuracy.

Other features, elements, steps, characteristics and advantages of the present invention will become more apparent from the following detailed description of preferred embodiments of the present invention with reference to the attached drawings.

DETAILED DESCRIPTION OF PREFERRED EMBODIMENTS

The present invention will now be clarified by describing preferred embodiments of the present invention with reference to the drawings.

Figure 1:
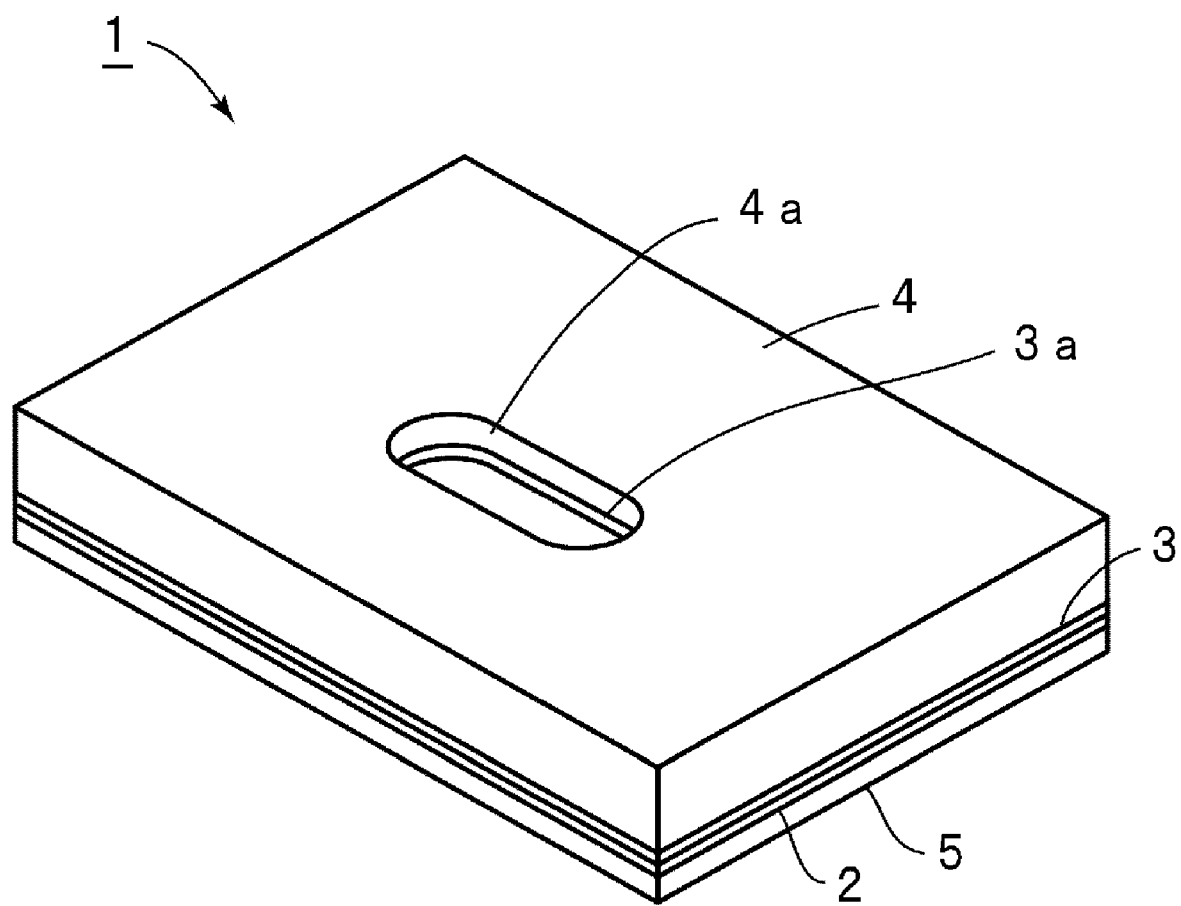
FIG. 1 is a perspective view showing an appearance of a sensor for detecting an analyte in liquid according to a first preferred embodiment of the present invention.
Figure 2:
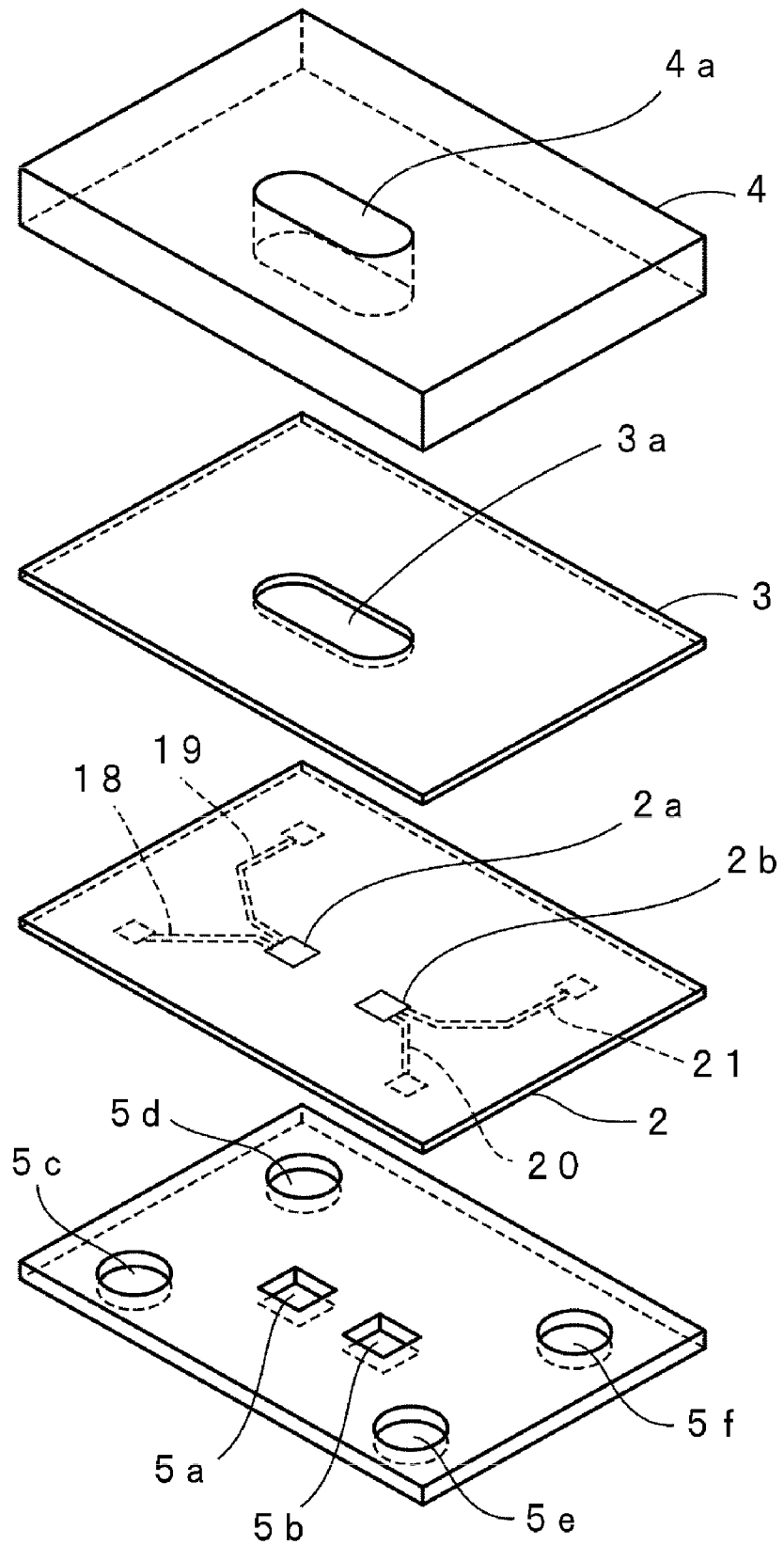
FIG. 2 is an exploded perspective view of the sensor according to the first preferred embodiment of the present invention.

FIG. 1 is a perspective view showing a sensor for detecting an analyte in liquid according to a first preferred embodiment of the present invention. FIG. 2 is an exploded perspective view of the sensor.

As shown in FIG. 2, the sensor 1 for detecting an analyte in liquid according to this preferred embodiment preferably includes a substantially rectangular plate-like base substrate. The base substrate 2 is preferably constructed of a suitable hard material such as a synthetic resin or ceramic. The base substrate 2 is provided with a plurality of openings 2a and 2b. In this preferred embodiment, the openings 2a and 2b are preferably substantially square in plan view. However, the shape is not limited to substantially and may be elliptical, for example, or other suitable shapes.

As shown in FIG. 2, on the top surface of the base substrate 2, a first adhesion layer 3 and a first protecting member 4 are stacked in this order. The first adhesion layer 3 and the first protecting member 4 are provided with substantially rectangular through-holes 3a and 4a, respectively. The through-holes 3a and 4a are arranged so as to overlap each other in the thickness direction. The opening portion provided by the overlapped through-holes 3a and 4a functions as a liquid-supplying opening and also as a liquid-trapping portion for trapping a supplied liquid.

The through-holes 3a and 4a are arranged so as to face the openings 2a and 2b of the base substrate 2. The first adhesion layer 3 tightly attaches the first protecting member 4 to the base substrate 2 and may be a rubber adhesive or other adhesive.

The first protecting member 4 is made of a hard material, such as a synthetic resin or ceramic. The through-hole 4a has a specific volume of space, so that the liquid to be supplied does not leak to the outside from the through-hole 4a and is securely injected into the openings 2a and 2b.

Furthermore, on the bottom surface of the base substrate 2, a second protecting member 5 is attached preferably via an adhesive. The second protecting member 5 is made of a hard material, such as a synthetic resin or ceramic, and has a plate-like shape. In addition, an adhesive, such as an epoxy adhesive or a rubber adhesive, may be optionally used.

As is shown in FIGS. 1 and 2, the planar shapes of the first adhesion layer 3, the first protecting member 4, and the second protecting member 5 are substantially the same as that of the base substrate 2. Consequently, the sensor 1 according to this preferred embodiment has an overall substantially rectangular plate-like shape. In addition, the second protecting member 5 is provided with concave portions 5a and 5b at regions corresponding to positions under the openings 2a and 2b. The concave portions 5a and 5b function as receiving portions by surrounding SAW elements described below. The concave portions 5a and 5b may have bottoms or may be through-holes. In order to protect the SAW elements, the depth of each of the concave portions 5a and 5b is greater than the thickness of the SAW elements.

Furthermore, the second protecting member 5 is provided with a pair of through-holes 5c and 5d near one short side and a pair of through-holes 5e and 5f near the other short side. The through-holes 5c to 5f are provided for inserting measurement pins therein when properties are measured.

In addition, it is not necessary that all of the base substrate 2, the adhesion layer 3, the protecting member 4, and the second protecting member 5 shown in FIG. 2 have the same planar dimension. For example, the base substrate 2 which is made of a relatively expensive material may have a small size, and other members which are made of inexpensive materials may have sizes suitable for handling. With that, a sensor for detecting an analyte in liquid, which is inexpensive and superior in handling, can be advantageously provided.

Figure 3A:
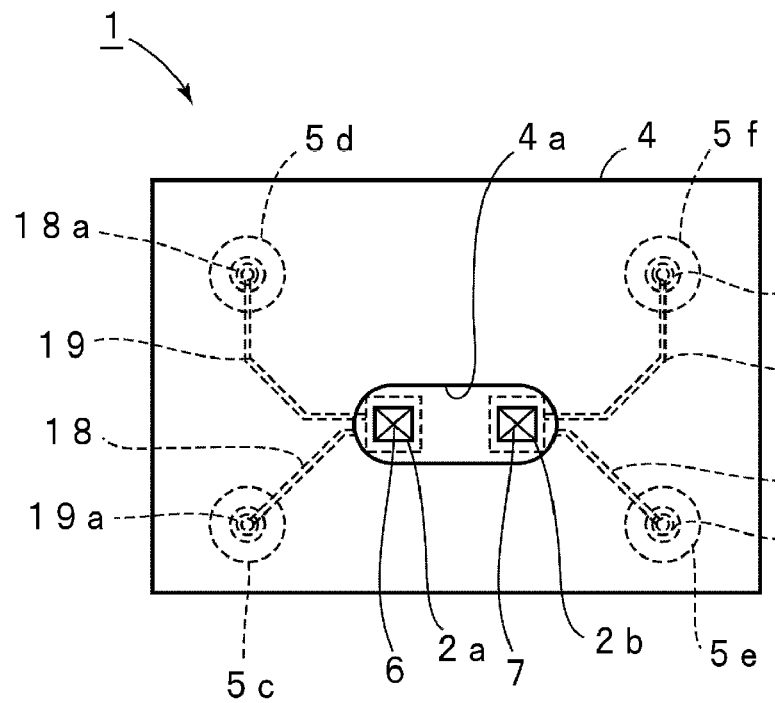
FIG. 3A is a plan view.
Figure 3B:
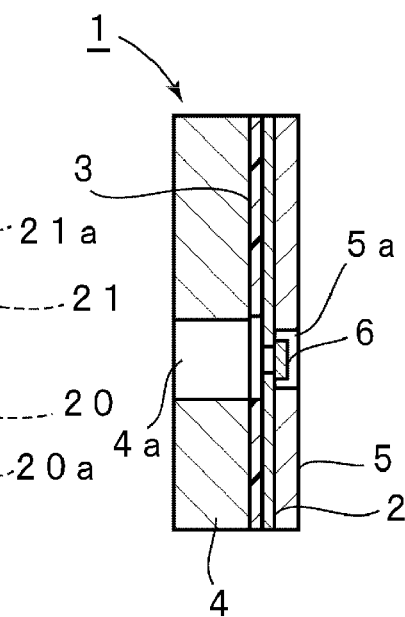
FIG. 3B is a lateral cross-sectional view.
Figure 3C:
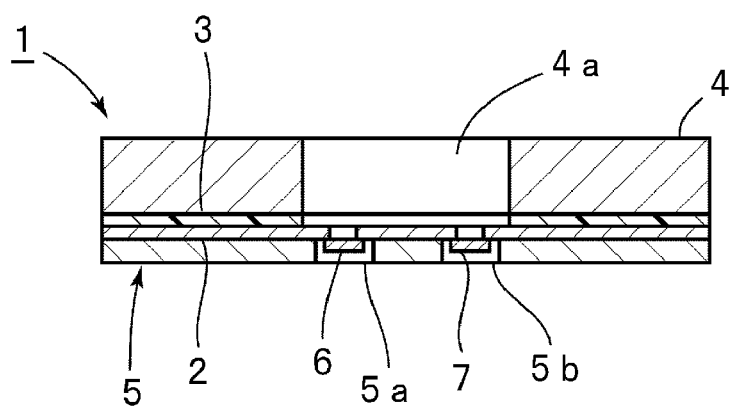
FIG. 3C is a front cross-sectional view of the sensor according to the first preferred embodiment of the present invention.

FIGS. 3A to 3C are a plan view, a lateral cross-sectional view, and a front cross-sectional view of the sensor 1. As shown in FIGS. 3B and 3C, first and second SAW elements 6 and 7 are mounted on the bottom surface of the base substrate 2, as a plurality of SAW elements. In FIG. 3A, the SAW elements 6 and 7 are schematically indicated by the x marks.

In FIGS. 3B and 3C, the mounting structure of the SAW elements 6 and 7 on the bottom surface of the base substrate 2 is illustrated in a simplified manner to facilitate understanding. As a representative of the SAW elements, the mounting structure of the SAW element 6 is shown in detail in FIG. 4A as a partially cutout enlarged front view of the SAW element 6.

Figure 4A:
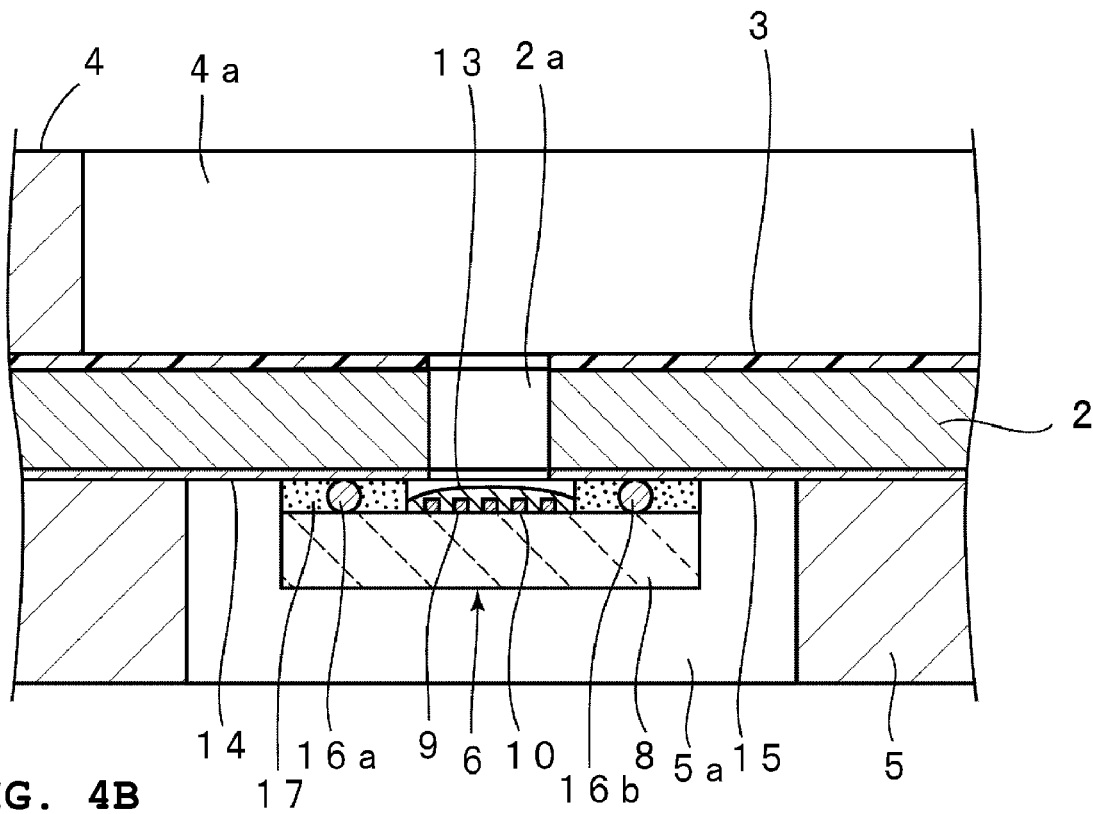
FIG. 4A is a partially cutout enlarged front cross-sectional view showing the details of a mounting structure of a SAW element of the sensor according to the first preferred embodiment.
Figure 4B:
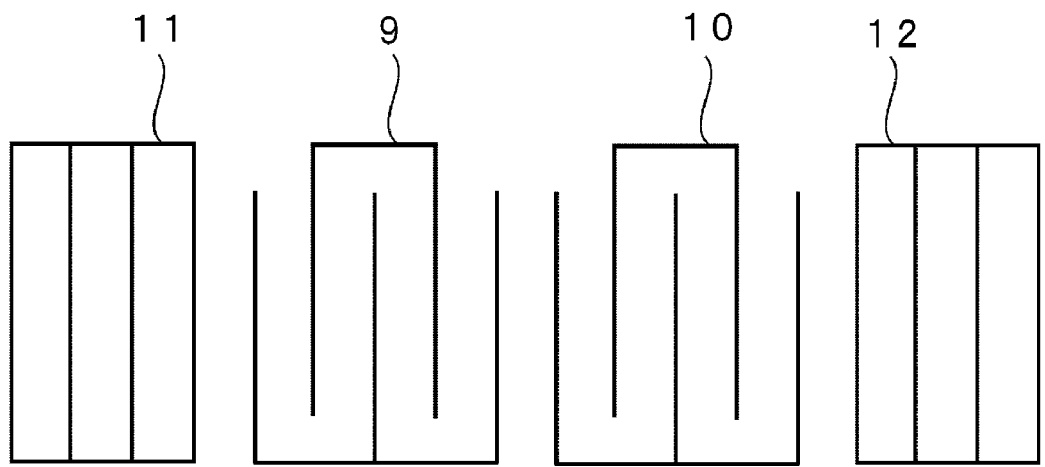
FIG. 4B is a plan view showing a structure of electrodes defining a sensing portion of the SAW element.

The SAW element 6 includes a piezoelectric substrate 8. The piezoelectric substrate 8 is preferably made of a piezoelectric single crystal or piezoelectric ceramic. On the top surface of the piezoelectric substrate 8, IDT electrodes 9 and 10 are provided. Further, reflectors are provided at both sides of the IDT electrodes 9 and 10 in the propagation direction of surface waves. In FIG. 4A, the region in which the IDT electrodes 9 and 10 are disposed is schematically illustrated. More specifically, as shown in FIG. 4B as a schematic plan view of the electrode structure, the IDT electrode 9 and the IDT electrode 10 are arranged in parallel in the propagation direction of surface waves. Furthermore, reflectors 11 and 12 are provided at both sides of the region where the IDT electrodes 9 and 10 are disposed. Thus, a resonator filter is provided.

In FIG. 4A described above, the region in which the IDT electrodes 9 and 10 are disposed defines as a sensing portion, and these IDT electrodes 9 and 10 are coated with a reaction membrane 13. The reaction membrane 13 includes a material which binds to an analyte in liquid. The reaction membrane 13 may be made of any material as long as the analyte can bind to the material on the surface of the reaction membrane 13. For example, the reaction membrane 13 includes a material which binds to a specific protein in a liquid. In such a case, the presence of the specific protein and concentration thereof can be detected or measured using the sensor 1 for detecting an analyte in liquid.

An example of the specific protein is bovine serum albumin, and an example of the reaction membrane 13 in such a case is N-2(aminoethyl)-3-aminopropyltrimethoxysilane [$(CH_3O)_3SiC_3H_6NHC_2H_4NH_2$].

The reaction membrane 13 may include a material which binds to an analyte other than proteins. Furthermore, the reaction membrane 13 may include only a material which binds to an analyte or may include a composition of a material which binds to an analyte and another base material which functions as a matrix.

As shown in FIG. 4A, the SAW element 6 includes the IDT electrodes 9 and 10 on the top surface of the piezoelectric substrate 8. Therefore, a sensing portion is provided on the top surface of the piezoelectric substrate 8. In this preferred embodiment, the SAW element 6 is mounted on the bottom surface of the base substrate 2 so that the sensing portion faces the opening 2a.

Furthermore, as shown in FIG. 4A, the SAW element 6 is connected to electrode lands 14 and 15 disposed on the bottom surface of the base substrate 2 via bump electrodes 16a and 16b. The bump electrodes 16a and 16b electrically connect the IDT electrodes 9 and 10 of the SAW element 6 to the electrode lands 14 and 15 and fix the SAW element 6 to the bottom surface of the base substrate 2.

In other words, the SAW element 6 is mounted on the bottom surface of the base substrate 2 by a flip-chip bonding method using the bump electrodes 16a and 16b. Therefore, in this preferred embodiment, the mounting structure of the SAW elements 6 and 7 on the base substrate 2 can be miniaturized as compared to that using a wire bonding method.

As the bump electrodes 16a and 16b, bump electrodes made of a metal, such as Au, may be optionally used.

The SAW element 7 is also mounted on the bottom surface of the base substrate 2 as in the SAW element 6. In addition, a resin layer 17 is provided for sealing the connection parts of the bump electrodes 16a and 16b. The resin layer 17 is hardened preferably using a thermosetting resin or a photosetting resin. Examples of the thermosetting or photosetting resin include epoxy resins and polyimide resins.

As shown in FIG. 2 and FIG. 3A, the electrode lands electrically connected to the SAW elements 6 and 7 are connected to wiring electrodes 18, 19, 20, and 21 disposed on the bottom surface of the base substrate 2. The wiring electrodes 18 and 19 are connected to the electrode lands 14 and 15 which are connected to the SAW element 6. The outside ends of the wiring electrodes 18 and 19 are connected to electrode pads 18a and 19a. As shown in FIG. 2, the electrode pads 18a and 19a are arranged at positions so as to overlap the through-holes 5c and 5d provided to the second protecting member 5. When measurement pins are inserted into the through-holes 5c and 5d, the measurement pins abut against the electrode pads 18a and 19a to allow the measurement.

Similarly, electrode pads 20a and 21a are provided at the outside ends of the wiring electrodes 20 and 21. The electrode pads 20a and 21a are located inside the through-holes 5e and 5f provided in the second protecting member 5.

The detection procedure using the sensor 1 for detecting an analyte in liquid according to this preferred embodiment will be described.

In a detection of an analyte in liquid, a liquid containing an analyte is supplied to the through-hole 4a of the first protecting member 4 as a liquid-supplying opening. The liquid may be supplied to the through-hole 4a by injecting or dropping the liquid with a syringe or pipette. As a result, the liquid is fed into the openings 2a and 2b through the through-holes 4a and 3a. Then, the liquid adheres to the sensing portions of the SAW elements 6 and 7 facing the openings 2a and 2b. When the sensing portion of the SAW element 6 is provided with a reaction membrane 13 and the liquid contains an analyte, the analyte binds to the reaction membrane 13 to induce a change. This change modifies the load applied to the sensing portion of the SAW element 6. Therefore, a difference in the load occurs between the load applied to a SAW element which is provided with the reaction membrane 13 and that applied to a SAW element which is not provided with the reaction membrane 13 as a standard. Consequently, the outputs of the SAW elements 6 and 7 are different from each other to allow the detection of the presence of the analyte and measurement of the concentration thereof.

Figure 6:
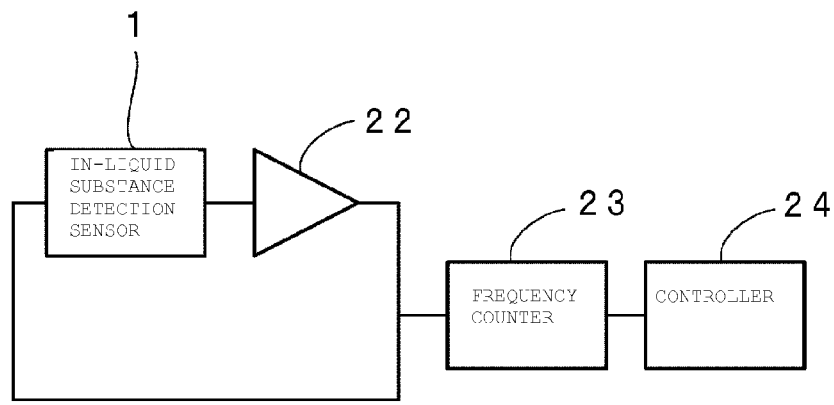
FIG. 6 is a block diagram for illustrating an example of a device for detecting an analyte in liquid using the sensor according to the first preferred embodiment of the present invention.

The device for detecting an analyte using the sensor 1 according to this preferred embodiment is not specifically limited. For example, as shown in FIG. 6, an amplifier 22 is connected to the output terminal of the sensor 1. The output of the amplifier 22 is connected to the input side of the sensor 1, and the output terminal of the amplifier 22 is connected to a frequency counter 23. The output terminal of the frequency counter 23 is connected to a controller 24. The controller 24 determines the presence or absence of a measurement result based on a signal from the frequency counter 23.

Figure 5A:
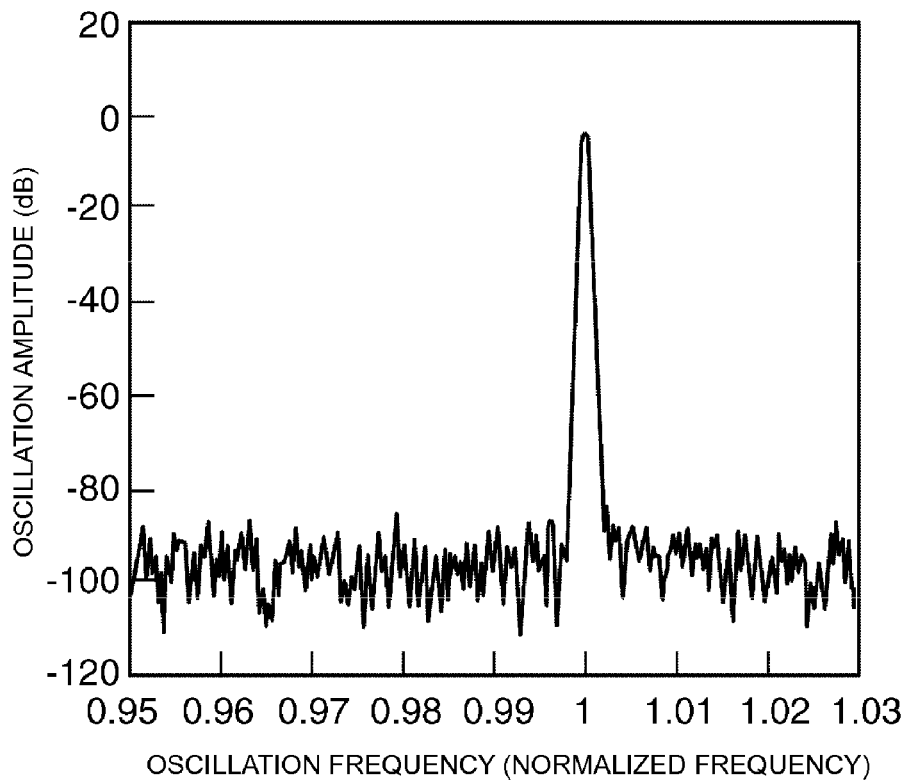
FIG. 5A is a graph showing a measurement result when the sensor for detecting an analyte in liquid according to the first preferred embodiment is used.

FIG. 5A is a graph showing output signals as a measurement result when saline containing bovine serum albumin is used as the liquid to be measured and the reaction membrane 13 includes a material which binds to the bovine serum albumin.

As shown in FIG. 5A, it is confirmed that the oscillation amplitude at the normalized oscillation frequency (frequency/resonance frequency of SAW element) is significantly large due to the presence of bovine serum albumin, and thereby the presence of bovine serum albumin can be detected with high accuracy.

Figure 5B:
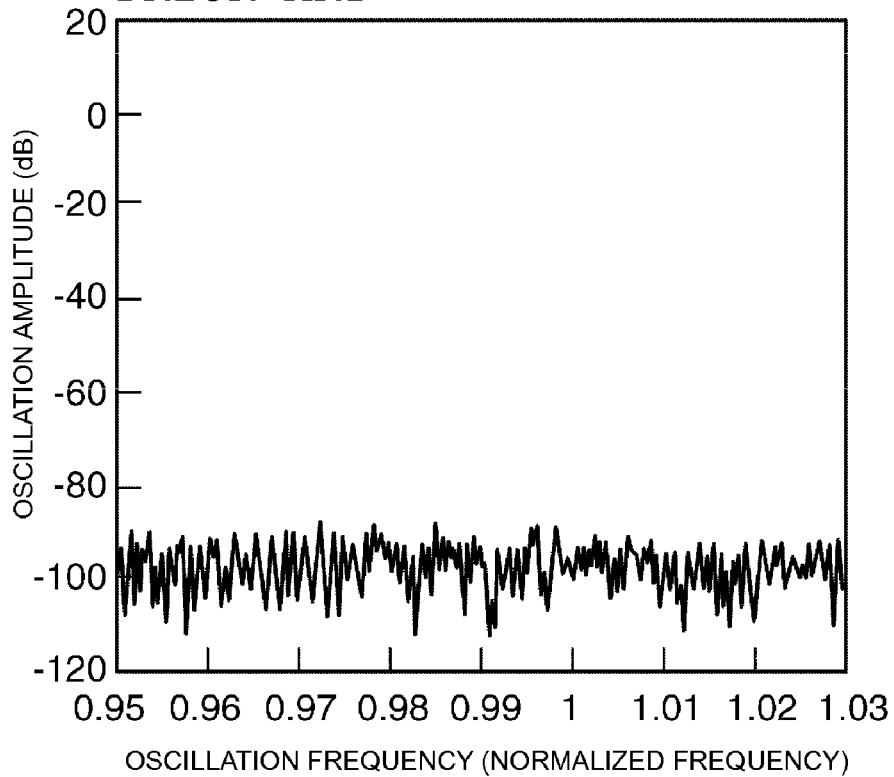
FIG. 5B is a graph showing a measurement result when a conventional sensor for detecting an analyte in liquid is used by immersing a surface acoustic wave element in a liquid sample.

In addition, a sensor for detecting an analyte in liquid, which includes a SAW element similar to the SAW element 6, is provided and immersed in saline containing bovine serum albumin as described above. FIG. 5B shows output signals when the measurement of a SAW element is performed in a state in which portions other than the sensing portion of the SAW element (portions other than the IDT, namely, wiring patterns, electrode pads, and so on) are exposed to the saline.

As shown in FIG. 5B, it is confirmed that bovine serum albumin is not detected because the measurement sensitivity is insufficient.

Figure 7:
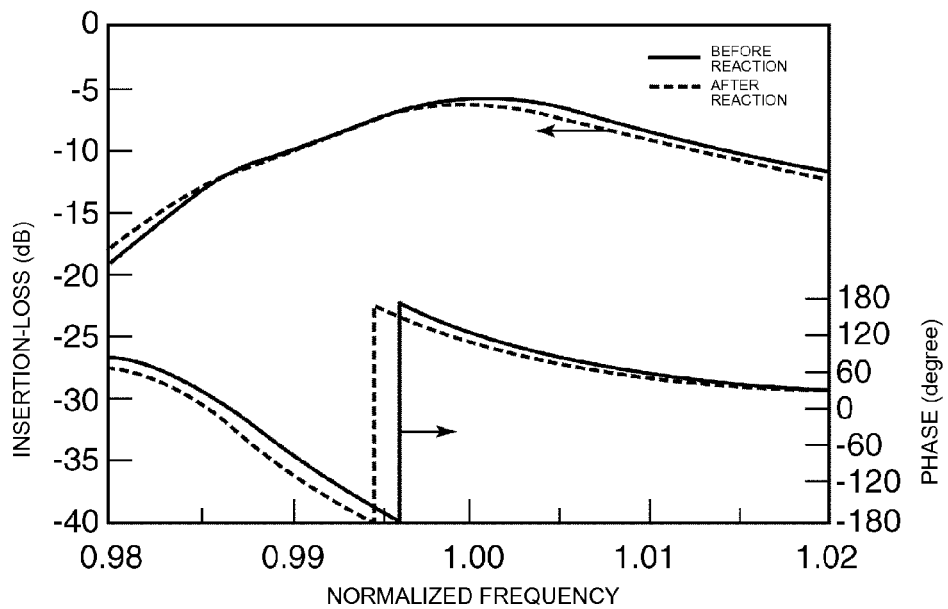
FIG. 7 is a graph for illustrating results obtained by measuring a saline containing bovine serum albumin with the sensor according the first preferred embodiment of the present invention.

FIG. 7 is a graph showing the measurement results when saline containing bovine serum albumin is measured using the sensor 1 according to the above-described preferred embodiment. The solid line in FIG. 7 shows before the reaction, namely, the result when saline not containing bovine serum albumin is supplied. The broken line shows the result when saline containing about 50 µg/ml of bovine serum albumin is measured. FIG. 7 shows the insertion-loss/frequency characteristic and phase/frequency characteristic. When saline containing bovine serum albumin is supplied, the characteristics of the SAW elements 6 and 7 are significantly changed. Here, the average characteristic between the SAW elements 6 and 7 is shown.

Figure 8:
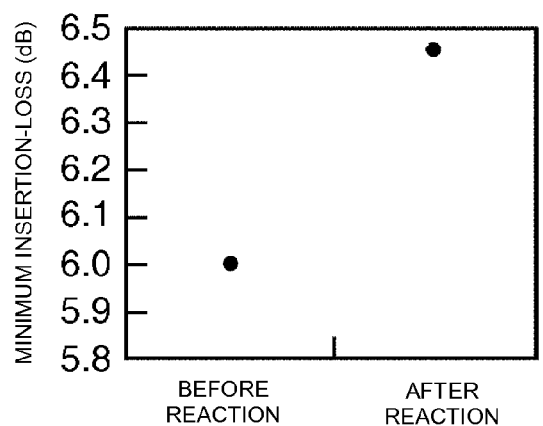
FIG. 8 is a graph showing a variation in minimum insertion-loss before and after the reaction in the measurement results shown in FIG. 7.
Figure 9:
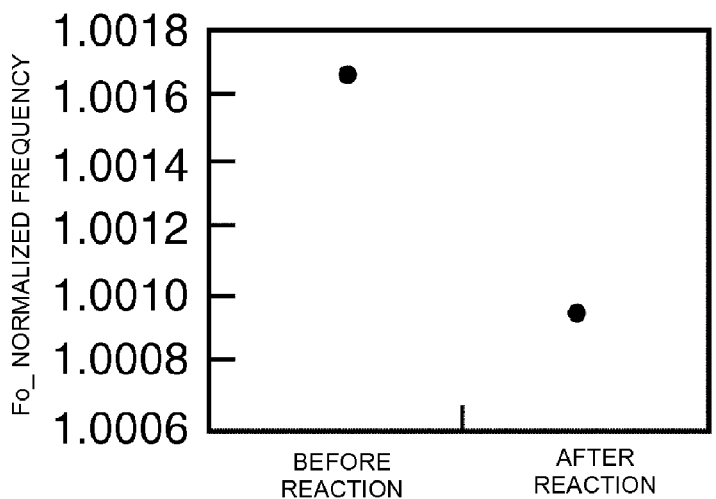
FIG. 9 is a graph showing normalized frequencies in the variation of the minimum insertion-loss before and after the reaction in the measurement results shown in FIG. 7.
Figure 10:
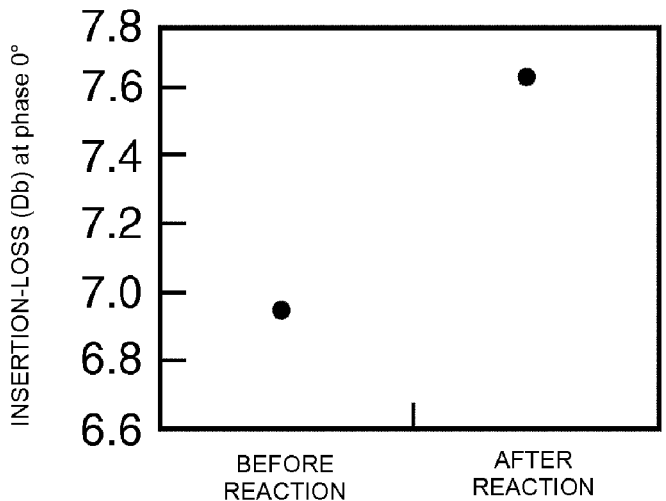
FIG. 10 is a graph showing a variation in insertion-loss at phase 0° before and after the reaction in the measurement results shown in FIG. 7.
Figure 11:
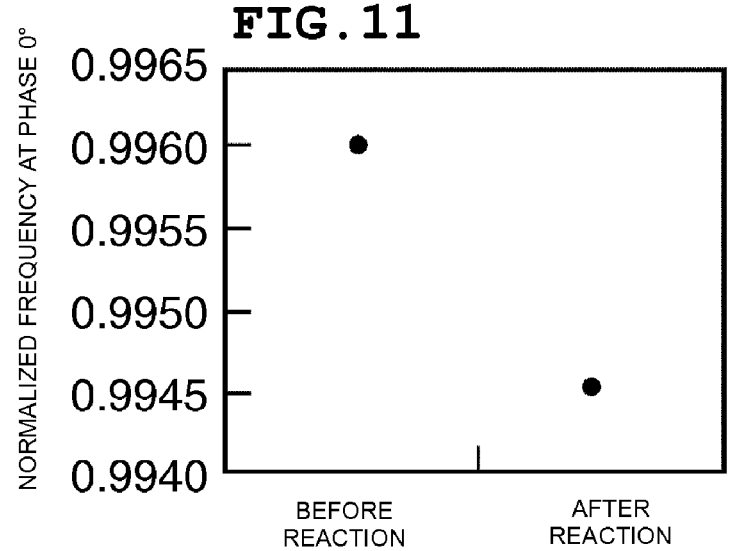
FIG. 11 is a graph showing a variation in normalized frequency at phase 0° before and after the reaction in the measurement results shown in FIG. 7.

In order to easily make comparison, the results shown in FIG. 7 are divided into the measurement results before the reaction and after the reaction and are shown in FIGS. 8 to 11. FIG. 8 shows the minimum insertion-loss. FIG. 9 shows the normalized frequency when the minimum insertion-loss largely changes. FIG. 10 shows the insertion loss at phase 0°. FIG. 11 shows the normalized frequency at phase 0°.

As shown in FIGS. 8 to 11, it is recognized that the minimum insertion-loss, normalized frequency when the minimum insertion-loss largely changes, insertion-loss at phase 0°, and normalized frequency at phase 0° are substantially changed between before and after the reaction. Therefore, it is confirmed that the presence of bovine serum albumin can be detected with high accuracy by detecting those changes.

Figure 12:
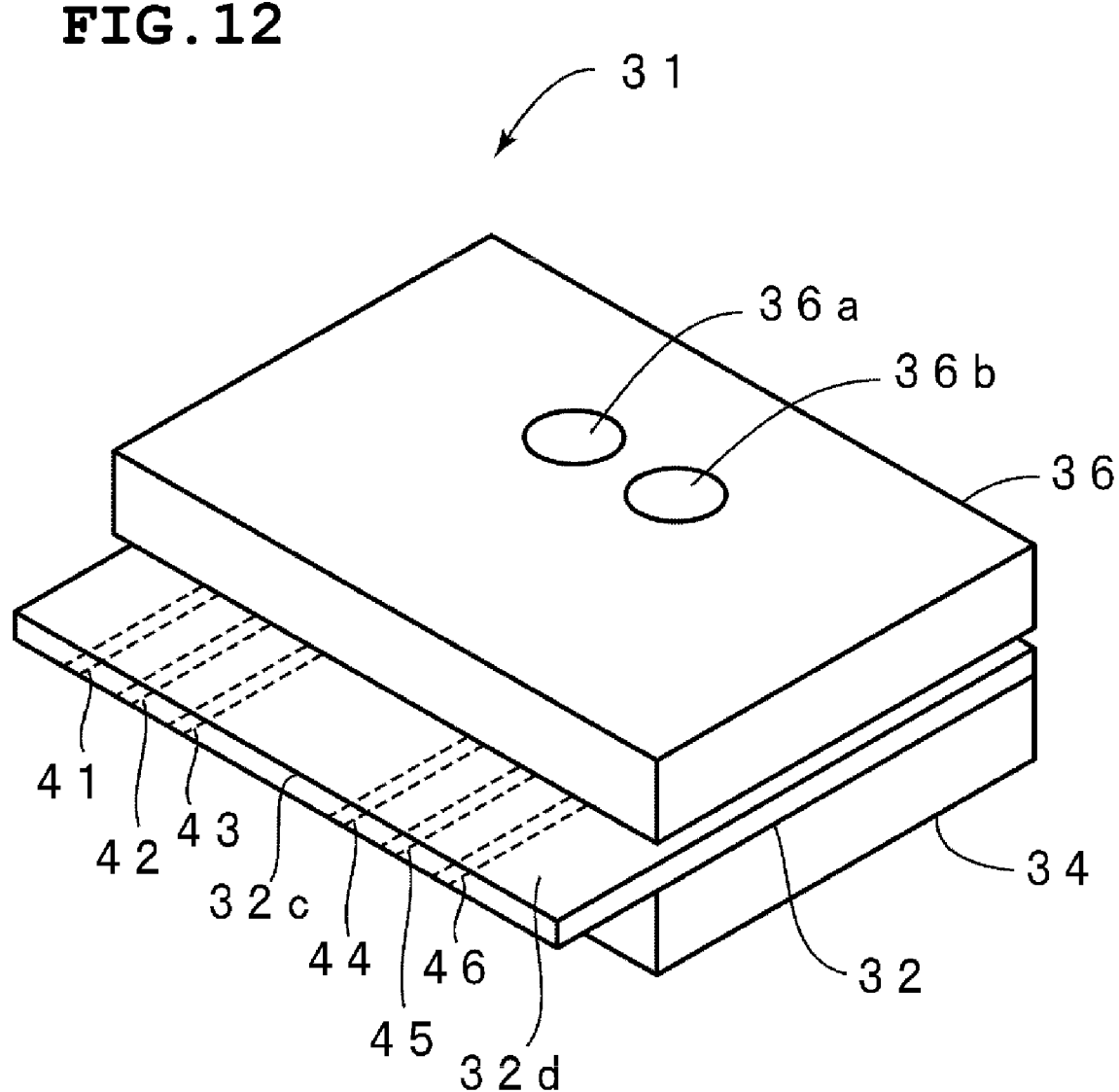
FIG. 12 is a perspective view showing an appearance of a sensor for detecting an analyte in liquid according to a second preferred embodiment of the present invention.
Figure 13:
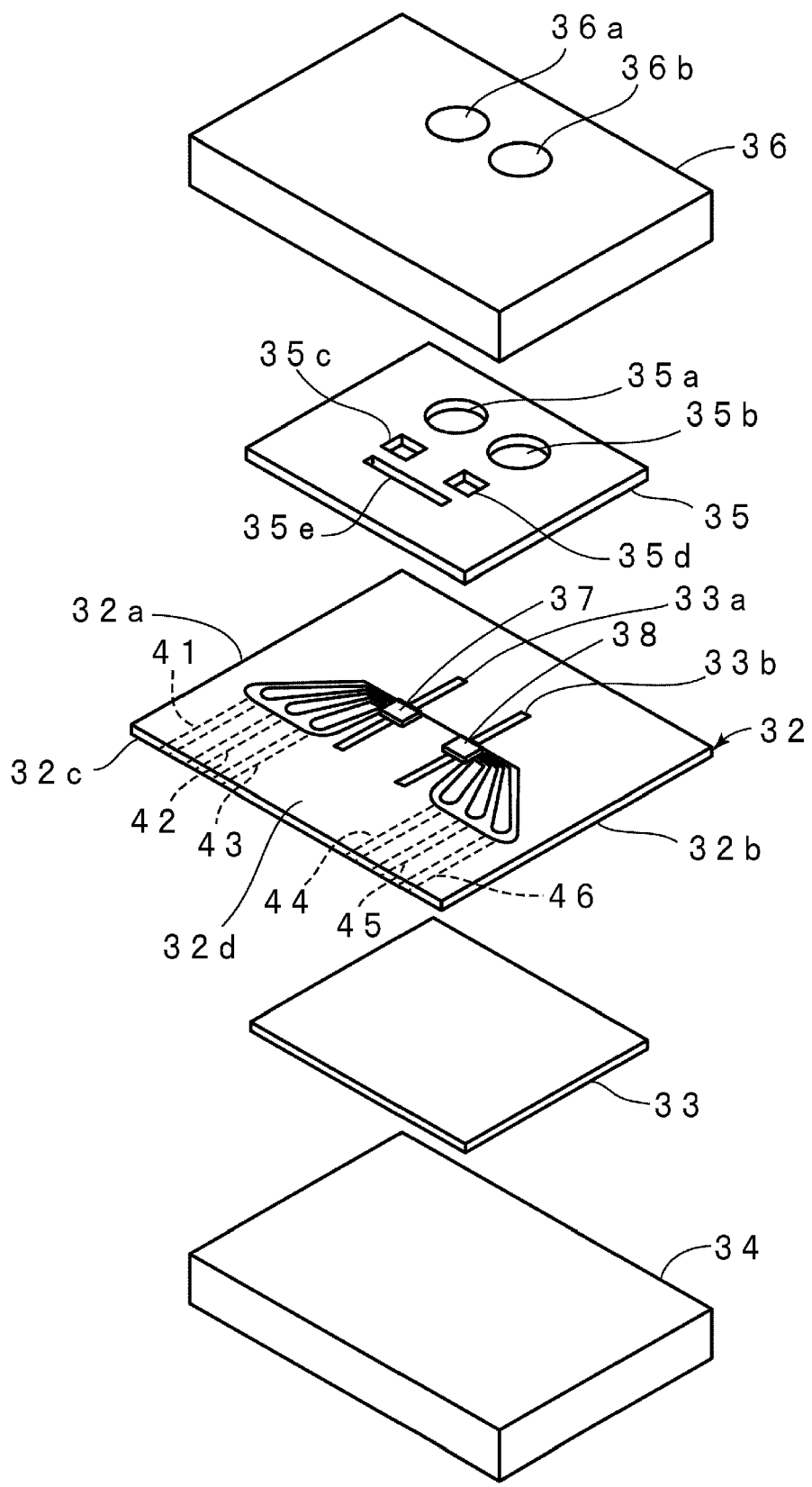
FIG. 13 is an exploded perspective view of the sensor according to the second preferred embodiment of the present invention.

FIG. 12 is a perspective view showing an appearance of a sensor for detecting an analyte in liquid according to a second preferred embodiment of the present invention. FIG. 13 is an exploded perspective view of the sensor.

In the sensor 31 for detecting an analyte in liquid according to the second preferred embodiment, a first adhesion layer 33 and a first protecting member 34 are stacked on the bottom surface of a base plate 32. Furthermore, on the top surface of the base plate 32, a second adhesion layer 35 and a second protecting member 36 are stacked in this order. In this preferred embodiment, SAW elements 37 and 38 are mounted on the top surface of the base plate 32 by a flip-chip bonding method. In other words, on the bottom surface (not shown in FIG. 13) of the base plate 32, IDT electrodes, reflectors, and a reaction membrane are arranged. In addition, the base plate 32 is provided with openings facing a sensing portion as in the first preferred embodiment, namely, sensing portions of the SAW elements 37 and 38 are arranged so as to face the openings.

In other words, the structure of the SAW elements 37 and 38 and the base plate 32 corresponds to a structure obtained by turning the base substrate 2 and the SAW elements 6 and 7 in the first preferred embodiment.

The lengths of the opposing sides 32a and 32b of the base plate 32 are greater than those of the first protecting member 34 and the second protecting member 36 in the same direction. Furthermore, on the bottom surface of the base plate 32, wiring electrodes 41 to 46 defining connecting electrodes to the outside are disposed. The wiring electrodes 41 to 46 are configured so as to extend to an end 32c of the base plate 32. As shown in FIG. 12, the end 32c of the base plate 32 protrudes further than the ends of the first protecting member 34 and the second protecting member 36. Therefore, in the sensor 31 according to this preferred embodiment, for example, the protruding portion 32d is inserted into a card insertion slot of a measurement device and thereby the wiring electrodes 41 to 46 are electrically connected to electrodes of the measurement device to enable the measurement.

As shown in FIG. 13 described above, the first protecting member 34 stacked on the first adhesion layer 33. In addition, the second protecting member 36 is disposed on the second adhesion layer 35. The second protecting member 36 is provided with through-holes 36a and 36b. The through-hole 36a functions as a liquid-supplying hole and the through-hole 36b functions as a liquid-discharging hole. The adhesion layer 35 is provided with through-holes 35a and 35b so that the through-holes 35a and 35b overlap the through-holes 36a and 36b, respectively. In addition, the adhesion layer 35 is provided with through-holes 35c and 35d so that the SAW elements 37 and 38 are surrounded by the through-holes 35c and 35d, respectively. Although not shown in the figure, concave portions for receiving the SAW elements 37 and 38 may be similarly provided on the bottom surface of the second protecting member 36.

Furthermore, the adhesion layer 35 is provided with a through-hole 35e extending substantially parallel to the direction connecting between the SAW elements 37 and 38.

The base plate 32 is provided with first channels 33a and 33b which face the through-hole 35e. The first channels 33a and 33b are formed by forming groove-like through-holes in the base substrate. One end of each of the first channels 33a and 33b is connected to the through-hole 35e. The other ends of the first channels 33a and 33b are connected to the through-hole 35a or 35b and the through-hole 36a or 36b, which are located above. Therefore, a liquid supplied to the through-hole 36a defining the liquid-supplying opening reaches the first channel 33a through the through-hole 35a. In addition, when the liquid flows in the first channel 33a, the liquid enters the bottom surface of the SAW element 37 from the opening located on the bottom surface of the SAW element 37 and is brought into contact with the sensing portion of the SAW element 37. Further, the liquid reaches the second channel 33b from the first channel 33a through the through-hole 35e defining a second channel. Then, the liquid is brought into contact with the sensing portion of the SAW element 38 exposing the liquid to an opening provided to the base substrate 32 at the second channel 33b and further flows to the through-hole 36b defining a liquid-discharging hole from the end of the channel 33b.

In order to achieve the above-described flow of a liquid, for example, the liquid is supplied to the through-hole 36a and discharged from the through-hole 36b by pressing the tip of a tube or pipette to the through-hole 36a and supplying a liquid into the through-hole 36a while applying a pressure to the liquid or by aspirating the liquid from the through-hole 36b.

In the sensor 31 for detecting an analyte in liquid according to this preferred embodiment, an analyte in liquid can also be measured by supplying a small amount of the liquid as in the first preferred embodiment. In addition, in this preferred embodiment, the end 32c of the base substrate 32 protrudes further than other members. Therefore, the measurement can be readily performed by inserting the protruding portion into a card insertion slot of a card-type measurement device.

Figure 14:
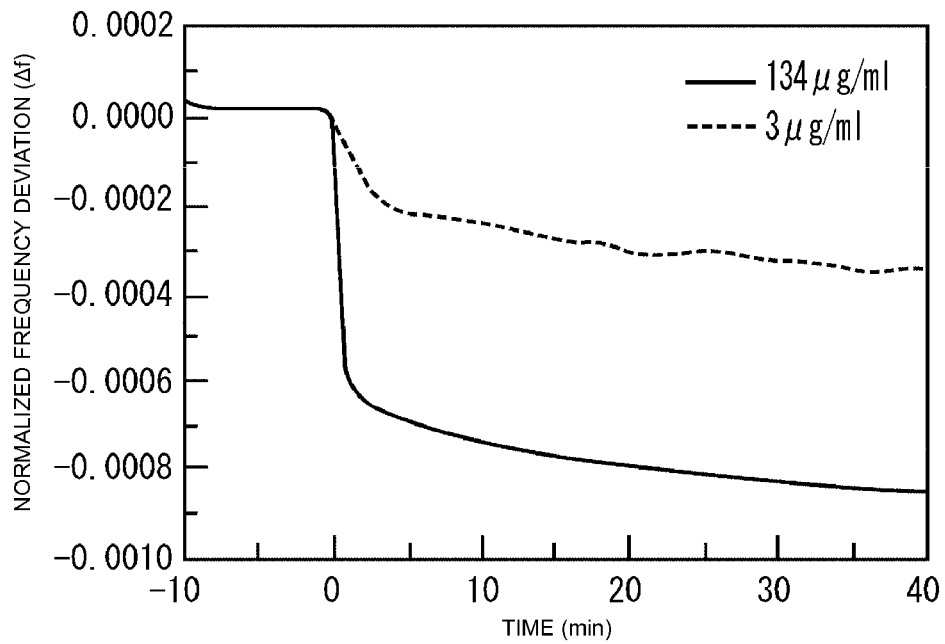
FIG. 14 is a graph showing a measurement result obtained by using the sensor according to the second preferred embodiment of the present invention.

FIG. 14 is a graph showing measurement results when the sensor for detecting an analyte in liquid according to the second preferred embodiment is used. In FIG. 14, the solid line shows the result obtained by measuring saline containing about 134 μg/ml of bovine serum albumin. The broken line shows the result obtained by measuring saline containing about 3 μg/ml of bovine serum albumin. As shown in FIG. 14, it is confirmed that the change in concentration of bovine serum albumin is extremely accurately detected based on a variation in the normalized frequency.

In the second preferred embodiment, two SAW elements 37 and 38 are used. However, as a modified example shown in FIG. 24, the SAW element may be a single SAW element 37A. In such a case, the SAW element 37A is provided with two IDTs as two sensing portions.

Figure 24:
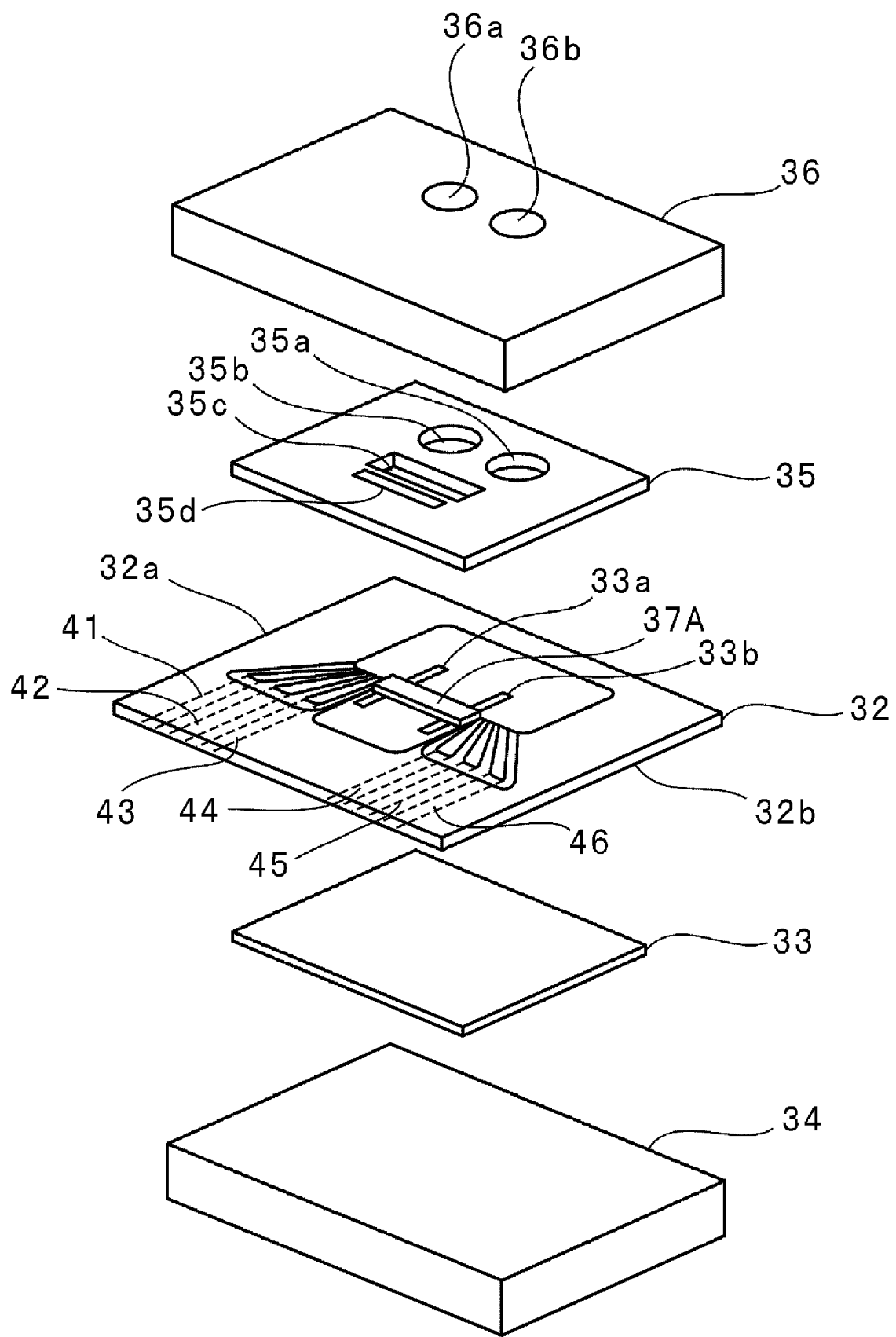
FIG. 24 is an exploded perspective view of a modification example of the sensor according to the second preferred embodiment of the present invention.
Figure 25:
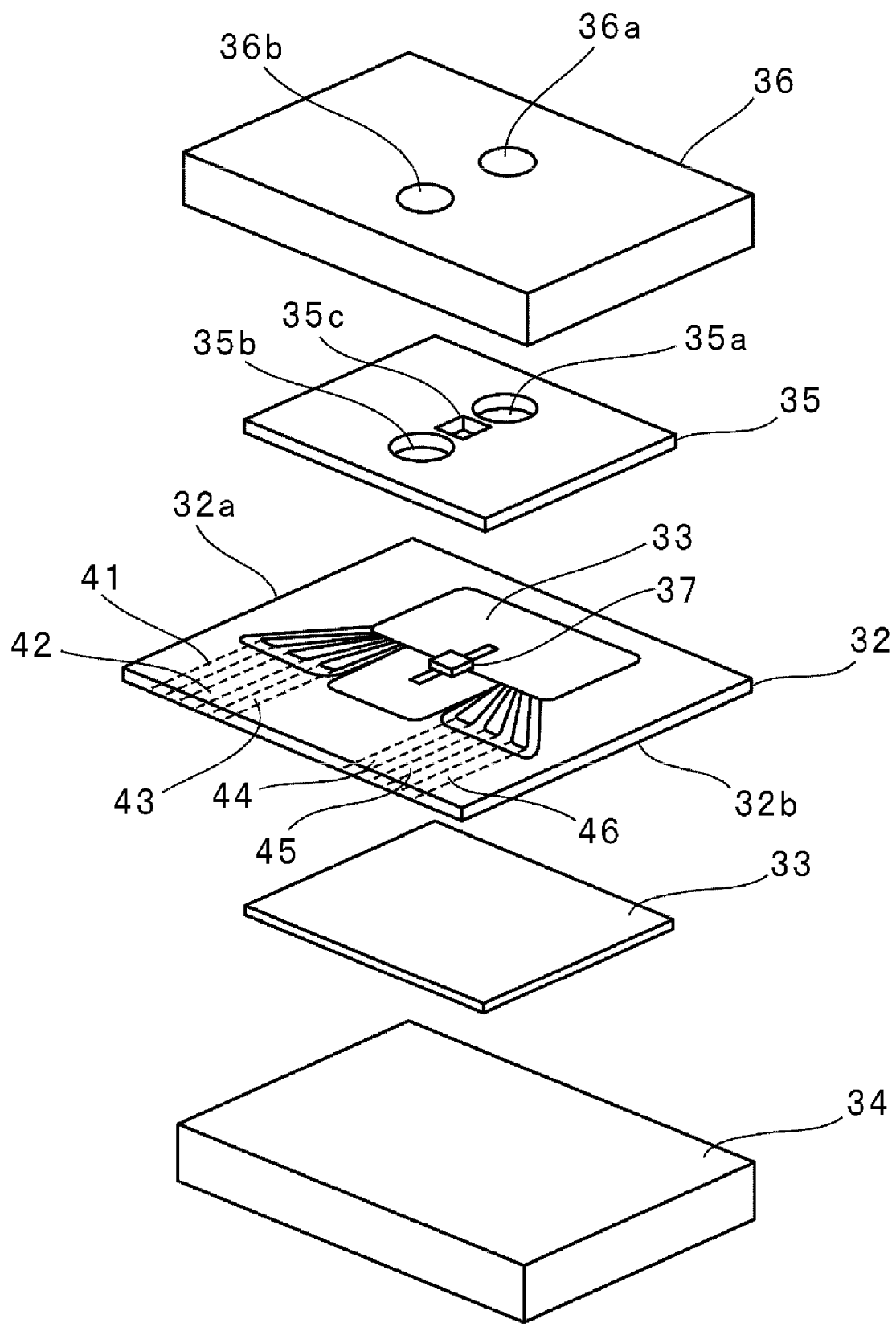
FIG. 25 is an exploded perspective view of another modification example of the sensor according to the second preferred embodiment of the present invention.

Furthermore, although two IDTs are provided as the sensing portions in the modified example shown in FIG. 24, the SAW may be a single SAW element 37 provided with only one IDT as the sensing portion as in a modified example shown in FIG. 25.

When a single element for sensing is used as in modified examples shown in FIGS. 24 and 25, the cost and size of the sensor can be decreased.

A sensor for detecting an analyte in liquid according to a third preferred embodiment will be described with reference to FIGS. 15 to 19. In this preferred embodiment, a sensor 51 for detecting an analyte in liquid is mounted on a measurement device 53 with a holding plate 52, which is separately shown in the upper side of the sensor 51 in the figure.

Figure 18:
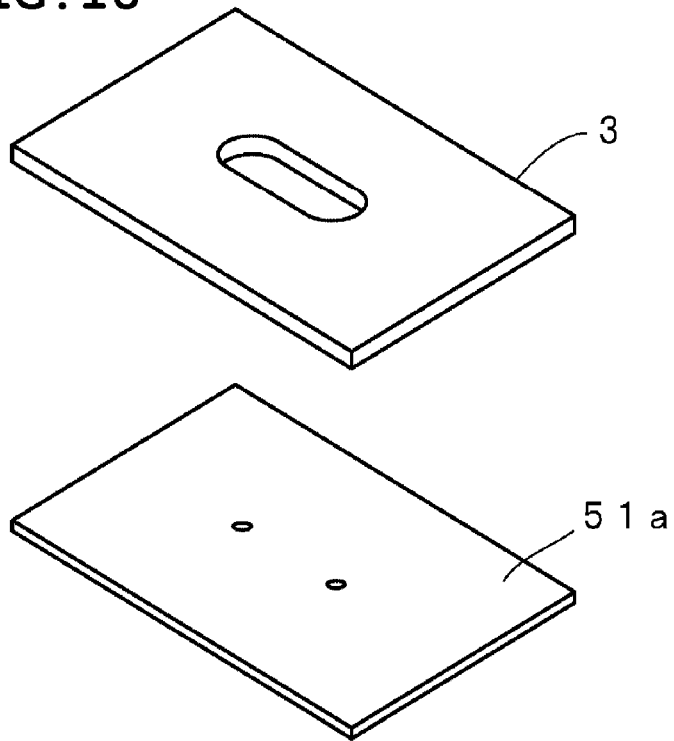
FIG. 18 is an exploded perspective view of the sensor for detecting an analyte in liquid according to the third preferred embodiment of the present invention.

FIG. 18 is an exploded perspective view for illustrating the sensor 51. The sensor 51 is provided with a base substrate 51a on which an adhesion layer 3 is fixed. On the rear surface of the base substrate 51a, SAW elements are mounted as in the sensor 1 in the first preferred embodiment.

The sensor 51 according to this preferred embodiment is configured as in the sensor 1 according to the first preferred embodiment except that the first protecting member 4 is not provided. Therefore, in the sensor 51, the first adhesion layer 3 is exposed to the upper surface. Since the sensor 51 is configured as in the sensor 1, the description for the first preferred embodiment is referred to here.

Figure 15:
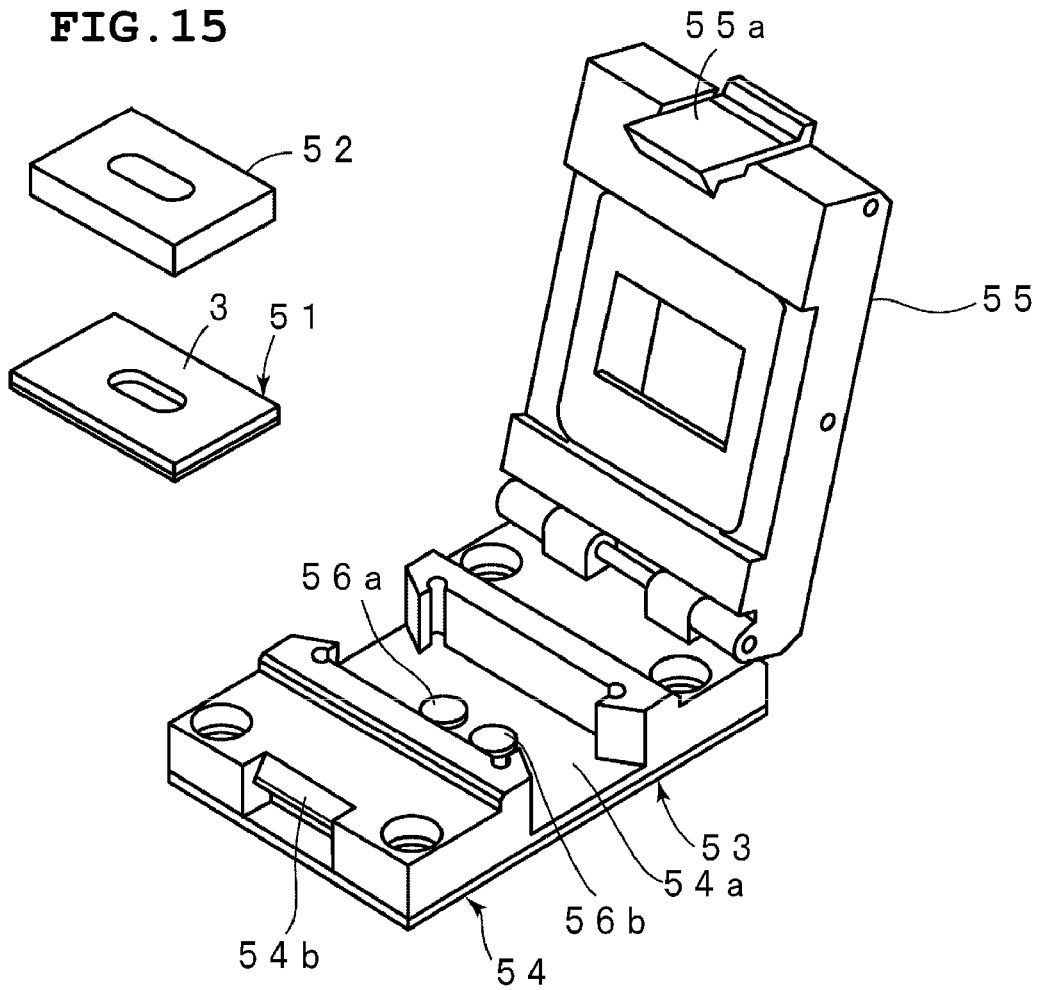
FIG. 15 is an exploded perspective view of a measurement device utilizing a sensor for detecting an analyte in liquid according to a third preferred embodiment of the present invention.

As shown in FIG. 15 described above, in this preferred embodiment, the measurement device 53 includes a base body 54 for mounting the sensor 51 thereon and a lid 55 which is attached to a connection part at one end of the base body 54 so as to be rotatable around the connection part as the center. Furthermore, the base body 54 is provided with a sensor-mounting portion 54a for mounting the sensor 51 thereon. The sensor-mounting portion 54a is provided with measurement probe pins 56a and 56b. The sensor 51 is mounted on the sensor-mounting portion 54a from above the measurement probe pins 56a and 56b.

In addition, above the sensor 51, a holding plate 52 is disposed. The holding plate 52 is similar to the first protecting member 4 provided to the sensor 1 according to the first preferred embodiment.

Figure 16:
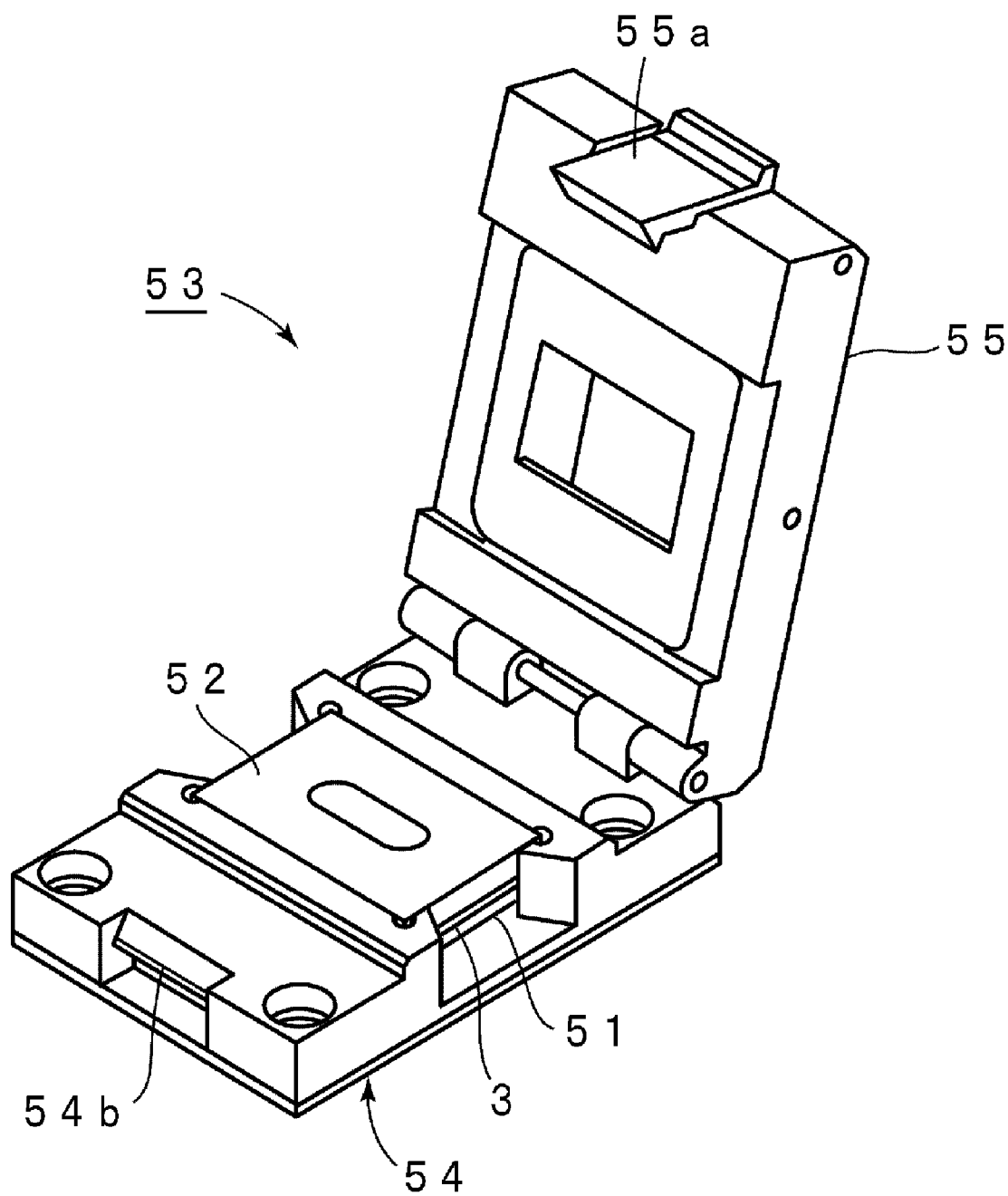
FIG. 16 is a perspective view showing a state in which a measurement device is provided with a sensor for detecting an analyte in liquid and a holding member.
Figure 17:
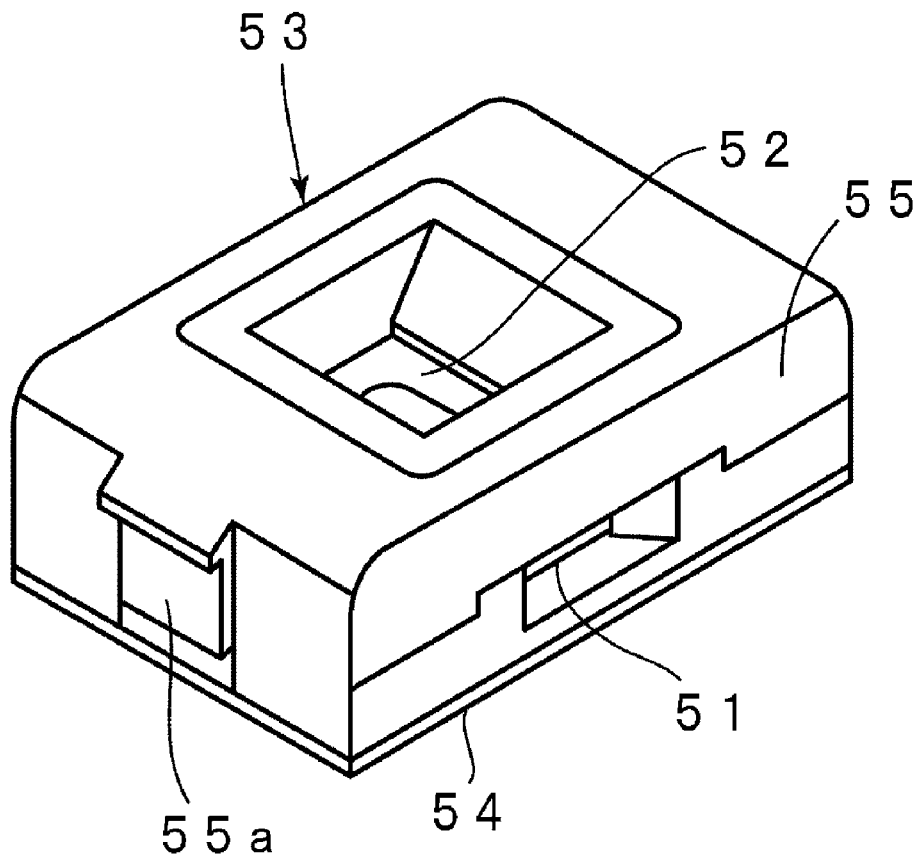
FIG. 17 is a perspective view of the measurement device shown in FIG. 16 in a state in which a lid is closed.
Figure 19:
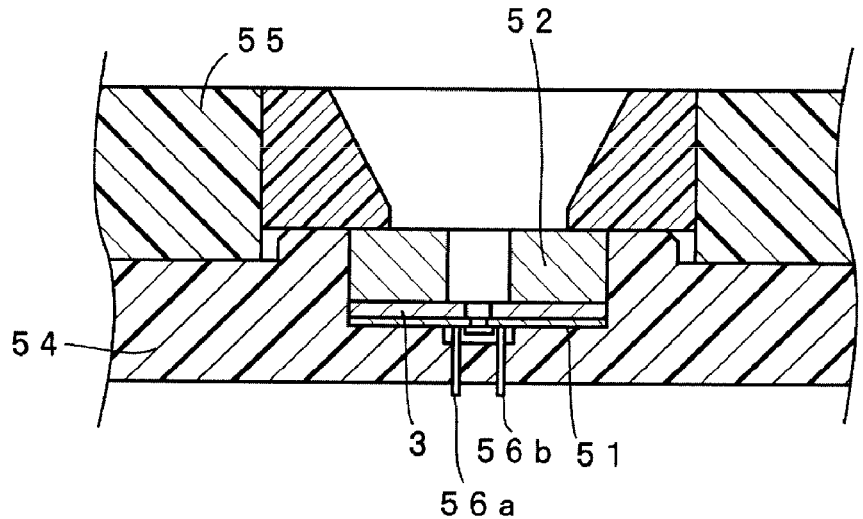
FIG. 19 is a front cross-sectional view showing a state in which the sensor according to the third preferred embodiment is mounted on a measurement device.

As shown in FIG. 16, the sensor 51 and the holding plate 52 are mounted on the device and then the lid 55 is rotated with the connection part so that a notch 55a provided at the end of the lid 55 is engaged with a protrusion 54b provided to one end of the base body 54. Thus, as shown in FIG. 17, the notch 55a of the lid 55 is engaged with the protrusion 54b to close the lid 55. As shown in FIG. 19, in the state in which the lid 55 is closed, the holding plate 52 is pressed onto the first adhesion layer 3. The thickness of the holding plate 52 is determined so that the holding plate 52 is pressed downward by the bottom surface of the lid 55. Therefore, the measurement probe pins 56a and 56b are securely abutted against the electrodes disposed on the bottom surface of the sensor 51 to allow the measurement.

As is obvious from this preferred embodiment, the sensor for detecting an analyte in liquid according to the present invention may not be provided with the first protecting member. In other words, a holding plate 52 may be used instead of the first protecting member. In addition, in some cases, the sensor may not be provided with the holding plate 52 when the thickness of the adhesion layer 3 is sufficiently increased.

The holding plate 52 may be optionally made of a rigid material, such as a metal, synthetic resin, or ceramic. In addition, the holding plate 52 may be made of an elastic material, such as rubber.

Furthermore, in cases in which the holding plate 52 is used or not, the first adhesion layer 3 is preferably made of an elastic material, such as a rubber sheet. With such a material, the first adhesion layer 3 is securely adhered to the upper and lower members by pressing from above. Thus, leakage of a liquid is prevented.

In addition, by controlling the thickness of the adhesion layer 3, the volume for trapping a liquid can be readily adjusted to a desired value.

In addition, the material for the adhesion layer 3 is not limited to elastic materials, such as rubber. An adhesive tape which is made of an adhesive agent provided on one surface of the backing material which is made of a synthetic resin film, such as polyethylene terephthalate, may be used as the adhesion layer 3.

When the sensor is not provided with the first protecting member, the number of components of the sensor itself is reduced. Therefore, the cost of the sensor for detecting an analyte in liquid is reduced. In addition, the holding plate 52 is not directly exposed to a liquid, and therefore, can be used repeatedly.

In FIG. 15, the holding plate 52 is prepared as a different member from the lid 55. However, the holding plate 52 may be fixed to the bottom surface of the lid 55 in advance. Furthermore, the bottom surface of the lid 55 may be integrally provided with a portion having the same function as that of the holding plate 52. In such cases, the number of the components is further reduced.

However, the holding plate 52 is preferably provided as a different member because the structure of the lid 55 can be simplified and the thickness of the holding plate 52 can be readily modified. Consequently, one measurement device 53 can be used for various types of sensors.

Figure 20:
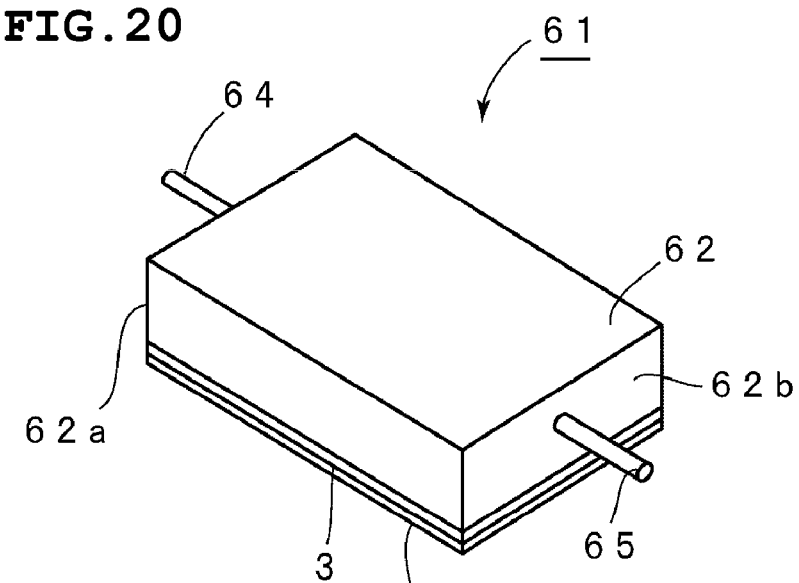
FIG. 20 is a perspective view showing a sensor for detecting an analyte in liquid according to a fourth preferred embodiment of the present invention.
Figure 21:
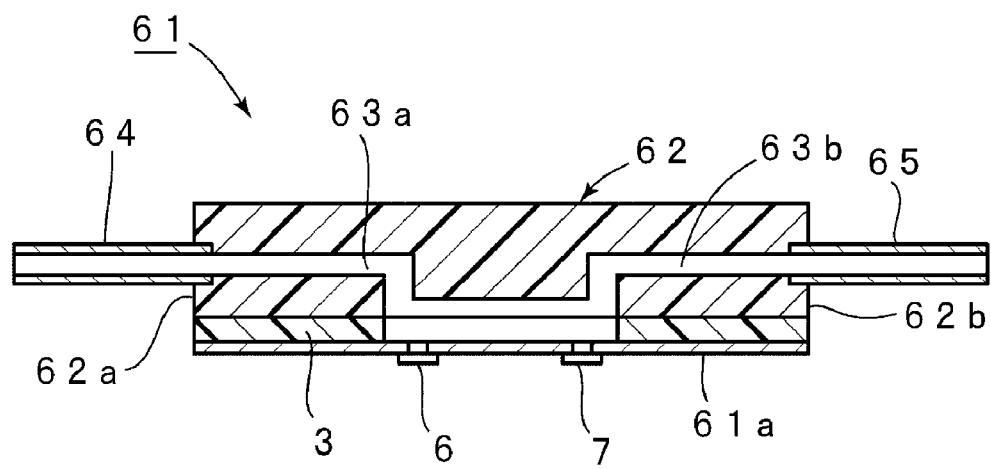
FIG. 21 is a perspective view showing a state in which the sensor according to the fourth preferred embodiment is mounted on a measurement device.
Figure 22:
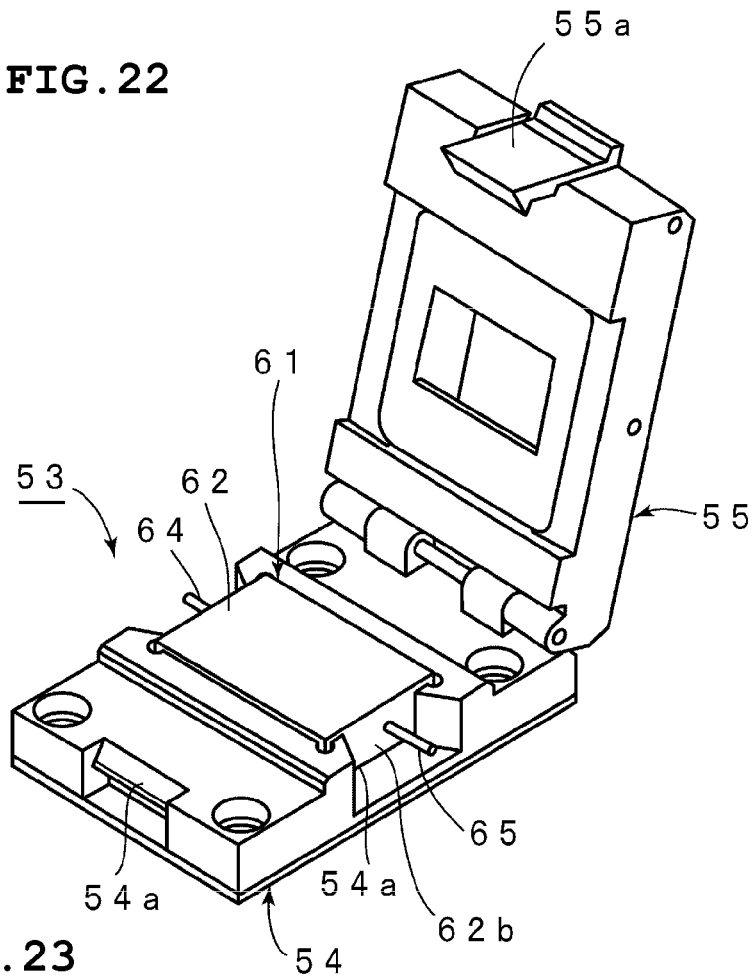
FIG. 22 is a front cross-sectional view of the sensor according to the fourth preferred embodiment of the present invention.
Figure 23:
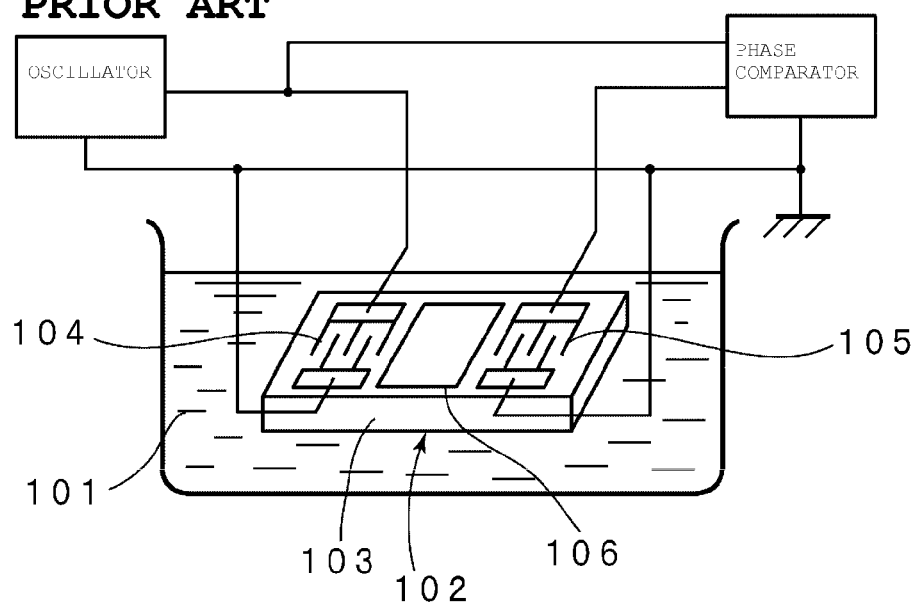
FIG. 23 is a schematic view for illustrating a conventional sensor for detecting an analyte in liquid.

FIGS. 20 to 22 are views for illustrating a sensor for detecting an analyte in liquid according to a fourth preferred embodiment. As shown in FIGS. 20 and 21, in this preferred embodiment, the sensor 61 for detecting an analyte in liquid includes a base substrate 61a, an adhesion layer 3 disposed on the base substrate 61a, and a holding plate 62 disposed on the adhesion layer 3. The adhesion layer 3 may be similar to the adhesion layer 3 in the first preferred embodiment. In addition, on the bottom surface of the base substrate 61a, SAW elements 6 and 7 are disposed. The structure at a portion where the base substrate 61a and the SAW elements 6 and 7 are disposed is substantially the same as that of the sensor 1 in the first preferred embodiment. Therefore, the description of the first preferred embodiment is referred to here.

In addition, the holding plate 62 is disposed on the adhesion layer 3. The holding plate 62 may be optionally formed of a material, such as a metal, synthetic resin, or ceramic. The sensor according to this preferred embodiment is provided with channels 63a and 63b in which a liquid as a measuring object flows. The inner ends of the channels 63a and 63b extend to a detection portion. The outer ends of the channels 63a and 63b extend to opposing end faces 62a and 62b of the holding plate 62. Tubes 64 and 65 are fixed to the end faces 62a and 62b. The tubes 64 and 65 are connected to the channels 63a and 63b. In this preferred embodiment, a liquid as a measuring object is supplied and discharged through the tubes 64 and 65. Therefore, the leakage of the liquid from the top surface of the holding plate 62 is prevented.

The sensor 61 according to this preferred embodiment can be used, as shown FIG. 22, by placing the sensor 61 on the sensor-mounting portion 54a of the measurement device 55 and then closing the lid 55. In this case also, electrodes disposed on the bottom surface of the sensor 61 can be securely abutted against the measurement probe pins 56a and 56b (refer to FIG. 15) by adding flexibility to the adhesion layer 3 or by adding flexibility to a portion of the holding plate 62.

Furthermore, in this preferred embodiment, two SAW elements are used, and one of the two SAW elements is provided with a reaction membrane. However, in the present invention, the number of the SAW elements may be one element or three or more elements.

For example, when first to third SAW elements, are used, the SAW elements are configured as follows: Among the first to third SAW elements, the first and second SAW elements are each provided with a reaction membrane and the third SAW element is not provided with a reaction membrane. In this case, the third SAW element functions as a reference. A liquid is supplied to the exposed first to third SAW elements and then frequencies are measured. A first frequency variation which is the difference between frequencies in the first SAW element and the third SAW element and a second frequency variation which is the difference between frequencies in the second SAW element and the third SAW element are determined. Then, the average of the first and second frequency variations is calculated. Using the average, the measurement accuracy in analyte measurement based on the frequency variation is increased.

In addition, in the sensor for detecting an analyte in liquid according to the second preferred embodiment shown in FIG. 13, the size of the opening of the base substrate 32 is larger than that of the SAW elements 37 and 38. However, in the sensor 51 shown in FIG. 18, the size of the opening of the base substrate 51a is smaller than that of the SAW elements 37 and 38. Thus, either the size of the SAW element or the size of the opening can be larger than the other.

While preferred embodiments of the present invention have been described above, it is to be understood that variations and modifications will be apparent to those skilled in the art without departing the scope and spirit of the present invention. The scope of the present invention, therefore, is to be determined solely by the following claims.

What is claimed is:

1. A sensor for detecting an analyte in liquid, the sensor comprising:
    a base substrate provided with at least one opening and an electrode land on a surface thereof at a periphery of the opening;
    a piezoelectric substrate, at least one SAW element including at least one IDT electrode and defining a sensing portion provided on the piezoelectric substrate, the piezoelectric substrate mounted on the base substrate so that the sensing portion of the at least one SAW element faces the at least one opening of the base substrate;
    a bump electrode connecting the at least one SAW element to the electrode land of the base substrate and mounting the at least one SAW element on the base substrate;
    a resin layer coating circumferences of the at least one SAW element and the bump electrode; and
    a reaction membrane selected to bind to an analyte and coating the surface of at least one sensing portion.

2. The sensor for detecting an analyte in liquid according to claim 1, wherein the at least one SAW element is a resonator SAW filter.

3. The sensor for detecting an analyte in liquid according to claim 1, wherein the reaction membrane binds to a specific protein.

4. The sensor for detecting an analyte in liquid according to claim 1, further comprising a first adhesion layer on a surface of the base substrate, the surface being at an opposite side of the surface on which the at least one SAW element is mounted.

5. The sensor for detecting an analyte in liquid according to claim 4, further comprising a first protecting member coating the first adhesion layer.

6. The sensor for detecting an analyte in liquid according to claim 1, further comprising a second protecting member fixed to the base substrate at the side on which the at least one SAW element is mounted, the second protecting member being provided with a concave portion for receiving the at least one SAW element.

7. The sensor for detecting an analyte in liquid according to claim 6, further comprising a second adhesion layer between the base substrate and the second protecting member.

8. The sensor for detecting an analyte in liquid according to claim 5, wherein the first protecting member is provided with a liquid-supplying opening, the liquid-supplying opening being connected to the opening of the base substrate.

9. The sensor for detecting an analyte in liquid according to claim 8, further comprising a first channel arranged to connect the liquid-supplying opening to the sensing portion of the at least one SAW element.

10. The sensor for detecting an analyte in liquid according to claim 9, wherein the first protecting member is provided with a liquid-discharging opening, and the sensor further comprises a second channel arranged to connect the liquid-discharging opening to the sensing portion of the SAW element.

11. A device for detecting an analyte in liquid, the device comprising:
- a sensor for detecting an analyte in liquid according to claim 1;
- an amplifier connected to the sensor and arranged to amplify output from the sensor;
- a frequency counter; and
- a controller.

* * * * *